(12) United States Patent
Tobin et al.

(10) Patent No.: US 6,388,172 B1
(45) Date of Patent: May 14, 2002

(54) PHYTOCHROME REGULATED TRANSCRIPTION FACTOR FOR CONTROL OF HIGHER PLANT DEVELOPMENT

(75) Inventors: Elaine Tobin, Los Angeles, CA (US); Lin Sun, Brookline, MA (US); Zhi-yong Wang, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 08/843,572

(22) Filed: Apr. 18, 1997

(51) Int. Cl.[7] .................... C12P 21/06; C07H 21/04; A01H 5/00; C12N 15/29
(52) U.S. Cl. .................... 800/290; 536/24.1; 435/69.1; 435/419; 800/278; 800/295; 800/298
(58) Field of Search .................... 536/24.1, 23.1, 536/23.6; 800/205, 278, 287, 290, 295, 298; 435/69.1, 468, 419

(56) References Cited

PUBLICATIONS

Smith et al. Nature. 1988 vol. 334: 724–726.*
Napoli et al. The Plant Cell. 1989. vol. 2: 279–289.*
Wang et al. Accession No.: PID g 1777443. NCBI. Jul., 1995.*
Valvekens et al. Proce. Natl. Acad. Sci. 1988. vol. 85: 5536–5540.*

* cited by examiner

Primary Examiner—Amy J. Nelson
Assistant Examiner—Ousama Zaghmout
(74) Attorney, Agent, or Firm—Daniel L. Dawes; Stefan J. Kirchanski

(57) ABSTRACT

The present invention involves the isolation and characterization of the first discovered phytochrome-regulated transcriptional factor, a protein designated CCA1 which binds to the promoter region of the chlorophyll binding protein gene (Lhcb1*3) of Arabidopsis. The Lhcb1*3 gene of Arabidopsis is known to be regulated by phytochrome in etiolated seedlings where a brief illumination by red light results in a large increase in the level of mRNA from this gene. A DNA binding activity, designated CA-1, that interacts with the promoter region of Lhcb1*3 was previously discovered in cellular extracts. This binding activity was used to obtain a cDNA clone for a transcription factor that binds specifically to the Lhcb1*3 promoter. Modification of the expression of CCA1 using techniques of genetic engineering results in unexpected changes in the timing of plant flowering. When CCA1 is overexpressed, it appears that the normal circadian rhythms of the plant are disrupted. The plants take a significantly longer time to reach flowering even in the presence of day length conditions that normally induce flowering. Thus, a method of extending vegetative growth and delaying flowering is provided.

4 Claims, 19 Drawing Sheets

```
        -160                                                                        -73
         |                                                                           |
A2   AATCTGCGAAGTGCGAGCCATTAACCACGTAAGCAACAAACAATCTAAACCCCAAAAAAATCTATGACTAGCCAATAGCAACCTCA
     TTAGACGCTTCACGCTCGGTAATTGGTGCATTCGTTGTTTGTTAGATTGGGGTTTTTTTTAGATACTGATCGGTTATCGTTGGAGT
                                 ** **    ***  *                ****
                                 _____                 _____
WT1  ------------------------------------------------------------------------------------
m1   -----------------------------G-GTT-------G-G-------------------G--T-C-------------
m2   -----------------------------G-GTT-------G-G-------------------------C-------------
m3   -----------------------------------------------------------------G--T-C-C-----------
m4   --------------------------A-----------------------------------------T---------------
WT2  --C-AA-CGATAA--C-----------TAA-A--..------GAATGA
                *                                  *

FIG. 1
```

```
G CAGTGGTTCA                                                                              -1000
CTTACAAGAA CCTGGTCTTC AAACCAGACA GGTTAACCAA TTCTCTCTTT AACTCTGTGT  -940
TTGGTTGCAT GTAATACTGA GAATGGAAGA CTCAAATTCT CGAGGAAATT GTTTGTTATC  -880
TGTTTCAGGG AGGCTTTGTT TGAGAAGGTC AAGAGCACAT ACAAAGACAT ATTAGGGAGC  -820
AGCTGAATCA AAGGAGGAAG AAGAGAAGA AGAGCCTTTT TGAGGCCATT CATGAATTGG   -760
AATGAAGGAT ATCAAAAGAA TCTAACACAA AGCCCACGTC CTTCCTTCAA TCTTTCCTTC  -700
TTGTAACTAA ATAATTTTCA TCCTTTCTCT CTCTCTGTCT CTGGTCTTTT TTAGCTCAAA  -640
GTATCATCCA TTTATGTCAA AGTGTTGTAA ATTCCTCAAG ACTATATATG AGATGTTTTG  -580
TTTCATTTTC CAAAATTTCA AACTTTGTCC CCATTTAGTC TTCTACCCTT CATGCATGGT  -520
TAGCTTAGCT TAATGCTGAA CTGTTGAATA ACGATATGGG CCTTATGCTA AAAGAACAAA  -460
ACCTTATGGG TCTAAAAAAA ATAAGCCCCAA TATAAAACTA TGGCCCAAAT AAGTTTAGGT  -400
CCATTAGAGT GTGAGAATAG CGCGTGTAGT GAACCGCACG TTCGATTGTT             -340
GGTGAAGTAG TCGTCTAGAT TCCCGGGTCC ACTGATGTTT CTAGTGTATC AGACACGTGT  -280
CGACAAACTG GTGGGAGAGA TTAACGATCT TAAGTAGGTC CCACTAGATC AAGATATAT   -220
AACGAATTGA CCTTTTTAAC CTTTCAGGTA GTCCCGGAAC TCGTGGCCTA GAATACAAAG  -160
AAGGTGTGA  ACAAGTTGAT GTTAAGATGG ACAAGAATGT AACTTGAACA AAAGCTGAAT  -100
CATCTCTTCA GCCACTAGTA TGTTGACATA TGGCAGTTTC TTTTGTAGCC TCGAAATAAA   -40
TAAATTAAAA AGTTTGAGGT TAAAGATAAT TATAGTGGCT GAGATTTCTC CATTTCCGTA    21
GCTTCTGGTC TCTTTCTTT GTTCATTGA TCAAAAGCAA ATCACTTCTT CTTCTTCTTC     81
TTCTCGATTT CTTACTGTTT TCTTATCCAA CGAAATCTGG AATTAAAAAT GGAATCTTTA   141
TCGAATCCAA GCTGATTTTG TTTCTTTCAT TGAATCATCT CTCTAAAGGT ACTTAAGATT   201
GATTATTGT  CATGGTCTTT CTTATTGTTT GATGAATAAC TTGACTTGAT TGTTTTTTGT   261
TTTGTGGATT AGTGGAATT  TGTAAAGAGA AGATCTGAAG TTGTGTAGAG GAGCTTAGTG   321
ATG GAG ACA AAT TCG TCT GGA GAA GAT CTG GTT ATT AAG GTAAATTAAC      370
```

FIG. 2A

```
Met Glu Thr Asn Ser Ser Gly Glu Asp Leu Val Ile Lys
 1               5                  10
TAAATTTTAG GGGGAAGATG ATTGTTTTAG GTGTCAAAGA TTGAGAATTT TAATGAAACT    430
TGATATAGAG ACT CGG AAG CCA TAT ACG ATA ACA AAG CAA CGT GAA AGG TGG   480
            Thr Arg Lys Pro Tyr Thr Ile Thr Lys Gln Arg Glu Arg Trp
             15                  20                  25
ACT GAG GAA GAA CAT AAT AGA TTC ATT GAA GCT TTG AGG CTT TAT GGT      528
Thr Glu Glu Glu His Asn Arg Phe Ile Glu Ala Leu Arg Leu Tyr Gly
           30                  35                  40
AGA GCA TGG CAG AAG ATT GAA G GTTGATTTTT ATTTCCCTTT ATATGTCTTA       580
Arg Ala Trp Gln Lys Ile Glu
 45             50
TTTTTGTGT TTGCAGAGGT TTGTCTTCAA ACTGATTGC TTTTTTTCAT TTGGACAG        638
AA CAT GTA GCA ACA AAA ACT GCT GTC CAG ATA AGA AGT CAC GCT CAG       685
Glu His Val Ala Thr Lys Thr Ala Val Gln Ile Arg Ser His Ala Gln
                   55                  60                  65
AAA TTT TTC TCC AAG GTAAAATCGG TTAAATTTGA AATGATGTTC TCATCTTCAT      740
Lys Phe Phe Ser Lys
         70
TGGCTTAATG CTTAAGACTT ATTGAAAGCC AGGCAAGTTT TCTGCTTCTT TTGCTTCTTA    800
GTCAGGAGAT AGATAGATTA CGTTTTTAGA GTTAGTAAT GAGCAATAAG TCTTAAAATA     860
GTTGGAGAAA TGACGAGATG TAATCGTTTT CTTTGTTTA TGCCTATATC TTGTTAATCC     920
ACAAACATGT ACATAGATTC TTCAGAAGAA TGTTAGTTTC TTTAGATTCT TCAGATAAAC    980
TTGTGTCTTC TTACCGATTC TGAGGTAGTG GCAAAAGTGG GCTGAGTGCT AGAAATTTTT   1040
```

*FIG. 2B*

```
GAATGTTCCT TGTGATAAGC CATAGAGGTA AACCATTTTT GATTTCCAG TTCTGTCATT      1100
TAAACTTGTT AGGTGTCATT AGATTTTTGT TTGTTTACGT TTGTTTAGAG GGTAACAAAA      1160
CTACTCTCAT CTCTCTCAG GTA GAG AAA GAG GCT GAA GCT AAA GGT GTA GCT      1212
                      Val Glu Lys Glu Ala Glu Ala Lys Gly Val Ala
                                          75                  80

ATG GGT CAA GCG CTA GAC ATA GCT ATT CCT CCA CGG CCT AAG CGT            1260
Met Gly Gln Ala Leu Asp Ile Ala Ile Pro Pro Arg Pro Lys Arg
                85                      90                  95

AAA CCA AAC AAT CCT TAT CCT CGA AAG ACG GGA AGT GGA ACG ATC CTT        1308
Lys Pro Asn Asn Pro Tyr Pro Arg Lys Thr Gly Ser Gly Thr Ile Leu
            100                     105                     110

ATG TCA AAA ACG GGT GTG AAT GAT GGA AAA GAG TCC CTT GGA TCA GAA        1356
Met Ser Lys Thr Gly Val Asn Asp Gly Lys Glu Ser Leu Gly Ser Glu
            115                     120                     125                 130

AAA GTG TCG CAT CCT GAG GTGATTTTCA TGGTCATATG GCATCTTTTT GCAGTGTGTC    1414
Lys Val Ser His Pro Glu
                135

ACATTGCTCC TCATGTTATT AATACAGATT GTGTGCTTCG TTTATAG ATG GCC AAT        1470
                                                    Met Ala Asn

GAA GAT CGA CAA CAA TCA AAG CCT GAA GAG AAA ACT CTG CAG GAA GAC        1518
Glu Asp Arg Gln Gln Ser Lys Pro Glu Glu Lys Thr Leu Gln Glu Asp
140                     145                     150                     155
```

FIG. 2C

```
AAC TGT TCA GAT TGT TTC ACT CAT CAG TAT CTC TCT GCT GCA TCC TCC    1566
Asn Cys Ser Asp Cys Phe Thr His Gln Tyr Leu Ser Ala Ala Ser Ser
                160                     165                 170

ATG AAT AAA AGT TGT ATA GAG ACA TCA AAC GCA AGC ACT TTC CGC GAG    1614
Met Asn Lys Ser Cys Ile Glu Thr Ser Asn Ala Ser Thr Phe Arg Glu
            175                     180                 185

TTC TTG CCT TCA CGG GAA GAG GTAAAAAACA ATCTTTCATT GCTATTTGAG       1665
Phe Leu Pro Ser Arg Glu Glu
        190

GTTTTAAGAC GATTAGTACT TTTCATGAAA CTAAAACCGT GGGGGAATAA CAG GGA     1721
                                                          Gly
                                                          195

AGT CAG AAT AAC AGG GTA AGA AAG GAG TCA AAC TCA GAT TTG AAT GCA    1769
Ser Gln Asn Asn Arg Val Arg Lys Glu Ser Asn Ser Asp Leu Asn Ala
                200                     205                 210

AAA TCT CTG GAA AAC GGT AAT GAG CAA GGA CCT CAG ACT TAT CCG ATG    1817
Lys Ser Leu Glu Asn Gly Asn Glu Gln Gly Pro Gln Thr Tyr Pro Met
            215                     220                 225

CAT ATC CCT GTG CTA GTG CCA TTG GGG AGC TCA ATA ACA AGT TCT CTA    1865
His Ile Pro Val Leu Val Pro Leu Gly Ser Ser Ile Thr Ser Ser Leu
                230                     235                 240

TCA CAT CCT CCT TCA GAG CCA GAT AGT CAT CCC CAC ACA GTT GCA GGA    1913
Ser His Pro Pro Ser Glu Pro Asp Ser His Pro His Thr Val Ala Gly
            245                     250                 255
```

*FIG. 2D*

```
GAT TAT CAG TCG TTT CCT AAT CAT ATA ATG TCA ACC CTT TTA CAA ACA    1961
Asp Tyr Gln Ser Phe Pro Asn His Ile Met Ser Thr Leu Leu Gln Thr
260             265                 270                 275

CCG GCT CTT TAT ACT GCC GCA ACT TTC GCC TCA TCA TTT TGG CCT CCC    2009
Pro Ala Leu Tyr Thr Ala Ala Thr Phe Ala Ser Ser Phe Trp Pro Pro
        280                 285                 290

GAT TCT AGT GGT GGC TCA CCT GTT CCA GGG AAC TCA CCT CCG AAT CTG    2057
Asp Ser Ser Gly Gly Ser Pro Val Pro Gly Asn Ser Pro Pro Asn Leu
            295                 300                 305

GCT GCC GCC ATG GCA GCC ACT GTT GCA GCT AGT GCT TGG TGG GCT        2105
Ala Ala Ala Met Ala Ala Thr Val Ala Ala Ser Ala Trp Trp Ala
                310                 315                 320

GCC AAT GGA TTA TTA CCT TTA CCT TTA TGT TGT TTT CCT CTT AGT TCA GGT TTC    2153
Ala Asn Gly Leu Leu Pro Leu Cys Phe Pro Leu Ser Ser Gly Gly Phe
        325                 330                 335

ACT AGT CAT CCT CCA TCT ACT TTT GGA CCA TCA TGT GAT GTA GAG TAC    2201
Thr Ser His Pro Pro Ser Thr Phe Gly Pro Ser Cys Asp Val Glu Tyr
340                 345                 350                 355

ACA AAA GCA ACT AGC ACT TTA CAA CAT GGT TCT GTG CAG AGC CGA GAG CAA    2249
Thr Lys Ala Ser Thr Leu Gln His Gly Ser Val Gln Ser Arg Glu Gln
                360                 365                 370

GAA CAC TCC GAG GCA TCA AAG GCT CGA TCT TCA CTG GAC TCA GAG GAT    2297
Glu His Ser Glu Ala Ser Lys Ala Arg Ser Leu Asp Ser Glu Asp
            375                 380                 385
```

FIG. 2E

```
GTT GAA AAT AAG AGT AAA CCA GTT TGT CAT GAG CAG CCT TCT GCA ACA      2345
Val Glu Asn Lys Ser Lys Pro Val Cys His Glu Gln Pro Ser Ala Thr
            390                 395                 400

CCT GAG AGT GAT GCA AAG GGT TCA GAT GGA GCA GGA GAC AGA AAA CAA      2393
Pro Glu Ser Asp Ala Lys Gly Ser Asp Gly Ala Gly Asp Arg Lys Gln
        405                 410                 415

GTT GAC CGG TCC TCG TGT GGC TCA AAC ACT CCG TCG AGT GAT GAT          2441
Val Asp Arg Ser Ser Cys Gly Ser Asn Thr Pro Ser Ser Asp Asp
420                 425                 430                 435

GTT GAG GCG GAT GCA TCA GAA AGG CAA GAG GAT GGC GGT ACC AAT GGT GAG  2489
Val Glu Ala Asp Ala Ser Glu Arg Gln Glu Asp Gly Gly Thr Asn Gly Glu
            440                 445                 450

GTG AAA GAA ACG AAT GAA GAC ACT AAT AAA CCT AAT ACG CAA ACT TCA GAG TCC  2537
Val Lys Glu Thr Asn Glu Asp Thr Asn Lys Pro Gln Thr Ser Glu Ser
        455                 460                 465

AAT GCA CGC CGC AGT AGA ATC AGC TCC AAT ATA ACC GAT CCA TGG AAG      2585
Asn Ala Arg Arg Ser Arg Ile Ser Ser Asn Ile Thr Asp Pro Trp Lys
    470                 475                 480

TCT GTG TCT GAC GAG GTACTTACTT GGACTAAAGA TCAACTTCCT TTATTTCAAA      2640
Ser Val Ser Asp Glu
    485

TCATTTTCTC ATATAAATAT TGTACATTCG GGT CGA ATT GCC TTC CAA GCT CTC     2694
                                Gly Arg Ile Ala Phe Gln Ala Leu
                                    490                 495
```

*FIG. 2F*

```
TTC TCC AGA GAG GTA TTG CCG CAA AGT TTT ACA TAT CGA GAA GAA CAC      2742
Phe Ser Arg Glu Val Leu Pro Gln Ser Phe Thr Tyr Arg Glu Glu His
                500                 505                 510

AGA GAG GAA CAA CAA CAA GAA CAA AGA GAA CAA AGA TAT CCA ATG GCA CTT  2790
Arg Glu Glu Gln Gln Gln Glu Gln Arg Glu Gln Arg Tyr Pro Met Ala Leu
        515                 520                 525

GAT CTT AAC TTC ACA GCT CAG TTA ACA CCA GTT GAT GAT CAA GAG GAG      2838
Asp Leu Asn Phe Thr Ala Gln Leu Thr Pro Val Asp Asp Gln Glu Glu
                530                 535                 540

AAG AGA AAC ACA GGA TTT CTT GGA ATC GGA TTA GAT GCT TCA AAG CTA      2886
Lys Arg Asn Thr Gly Phe Leu Gly Ile Gly Leu Asp Ala Ser Lys Leu
545                 550                 555                 560

ATG AGT AGA GGA AGA ACA GGT TTT AAA CCA TAC AAA AGA TGT TCC ATG      2934
Met Ser Arg Gly Arg Thr Gly Phe Lys Pro Tyr Lys Arg Cys Ser Met
        565                 570                 575

GAA GCC AAA GAA AGT AGA ATC CTC AAC AAC AAT CCT ATC ATT CAT GTG      2982
Glu Ala Lys Glu Ser Arg Ile Leu Asn Asn Asn Pro Ile Ile His Val
                580                 585                 590

GAA CAG AAA GAT CCC AAA CGG ATG GAA ACT CAA GCT TCC ACA              3030
Glu Gln Lys Asp Pro Lys Arg Met Glu Thr Gln Ala Ser Thr
        595                 600                 605

TGAGACTCTA TTTTCATCTG ATCTGTGTT TGTACTCTGT TTTTAAGTTT TCAAGACCAC     3090
TGCTACATTT TCTTTTTCTT TTGAGGCCTT TGTATTGTT TCCTTGTCCA TAGTCTTCCT    3150
GTAACATTTG ACTCTGTATT ATTCAACAAA TCATAAACTG TTTAATCTTT TTTTTTCCAA    3210
CCTGGAAAGA ACTTCACTCA AGGGGCTCTT GTTCTTGATA TATGCAAACG ACAGAGTTCC    3270
AAAACGTAAT CTTAGCCCAT CCATCACCCT TAAGTTGTCT CATAACTCAT AAGTAAGCAC    3330
AAAA
```

FIG. 2G

```
                                                                              aa
CCA1    RERWTEEEHNRFIEALRLYGR-AWQKIEEH-VATKTAVQIRSHAQKFF-SKVEKE                75
St1     GVPWTEEEHRMFLLGLGKLGKGDWRGIARNYVISRTPTQVASHAQKYEIRQSNMS                155
HMyb    KTSWTEEEDRIIYQAHKRLGN-RWAEIAKL-LPGRTDNAIKNHWNSTMRRKVEQE                196
CMyb    KTSWTEEEDRIIYQAHKRLGN-RWAEIAKL-LPGRTDNAIKNHWNSTMRRKVEQE                196
DMyb    KTAWTEKEDEIIYQAHLELGN-QWAKIAKR-LPGRTDNAIKNHWNSTMRRKYDVE                240
ZmC1    RGNISYDEEDLIIRLHRLYGN-RWSLIAGR-LPGRTDNEIKNYWNSTLGRRAGAG                121
YBAS1   LREWTLEEDLNLISKVVKAYGT-KWRKISSE-MEFRPSLTCRNRWRKII-TMVVRG               220
AtG11   KGNFTEQEEDLIIRLHKLLGN-RWSLIAKR-VPGRTDNQVKNYWNTHL-SKKLVG                120
```

FIG. 3

PHYTOCHROME REGULATED TRANSCRIPTION FACTOR FOR CONTROL OF HIGHER PLANT DEVELOPMENT

This invention was made with Government support under Grant No. GM23167 awarded by NIH. The Government has certain rights in this invention.

BACKGROUND OF THE INVENTION

1. Field of the Invention

The present invention concerns the field of genetic engineering and more particularly the discovery of a unique light-regulated transcription factor that can be used to control the flowering time of plants.

2. Background of the Invention

The Sun is the primary source of energy on the Earth. It is obvious that impinging solar energy warms our atmosphere and drives the Earth's climate. Perhaps less obvious is that virtually all biological energy including the "fossil" fuels that power our civilization are solar in origin. Solar energy is captured for biological use by photosynthesis, a metabolic process that occurs in green plants. During photosynthesis light energy is captured in various chemical compounds that provide food for all nonphotosynthetic organisms.

Since green plants essentially "feed" on light, it comes as no surprise that these organisms are exquisitely sensitive to light. Many people are aware that plants grow towards a light source in an effort to receive sustaining illumination. However, a green plant's responsiveness to light is much more complex than merely growing towards a light source. Plants contain complex systems for actually measuring the duration of day and night lengths so as to synchronize their growth and lifecycles with the seasons. It is these timing processes that cause chrysanthemums to flower in the autumn and other ornamental and crop plants to flower and fruit at characteristic times. Clearly, the ability to accurately control flowering to promote it or delay it as necessary would be of great economic value. In the middle decades of this century a tremendous amount of biological research was carried out in search of the ever elusive "flowering hormone" orfiorigen which, for a time, was the holy grail of plant physiology. Although the quest for florigen ended in failure, much was learned about how plants perceive and respond to environmental factors such as the seasonal changes in day length.

Although green plants have multiple light receptors, the protein-pigment phytochrome has been shown to be the primary receptor by which plants track day length and orchestrate a number of light-regulated responses. Phytochrome is a chromoprotein formed by combining a linear tetrapyrolle pigment with an apoprotein. As such it shows some similarities to phycobiliproteins which are accessory pigments of certain algae and photosynthetic bacteria. Phytoclirome has the somewhat unusual property of existing in two different photochemically interconvertible forms know as Pr (phytochrome-red) and Pfr (Phytochrome-far red). Phytochrome is synthesized in the Pr form which has an absorption maximum in the red region of the optical spectrum. Numerous experiments have shown that the Pr form of phytochrome is essentially inactive in terms of eliciting changes in plant metabolism. However, when Pr absorbs red light (R), it is rapidly converted into the active Pfr form. Pfr has an absorption maximum in the far red (near infrared) portion of the optical spectrum. Absorption of far red light (FR) induces a back conversion of Pfr to inactive Pr. This red-far/red interaction provides a powerful test of whether a given plant response is phytochrome mediated. For example, if dark-grown (etiolated) seedlings are briefly exposed to red light, Pfr will be formed and there will be a concomitant response. However, if the red light exposure is quickly followed by a far-red light exposure (which converts Pfr to inactive Pr) the response will be prevented. The reversibility of a red light response by a far-red light exposure is a hallmark of a phytochrome response.

Although much is known about the phytochrome proteins and their encoding genes, relatively little is known about how the Pfr effects a response in the plant. Many plant genes are light-regulated and that at least some of this regulation is controlled or influenced by phytochrome. Among the genes whose expression is either negatively or positively influenced by phytochrome are several that have been shown to be transcriptionally regulated. These genes include those encoding the small subunit of ribulose bisphosphate carboxylase/oxygenase, the major light-harvesting chlorophyll a/b binding-proteins (Lhcb) of Photosystem II, NADPH: protochlorophyllide oxioreductase, ferredoxin and phosphoenolpyruvate carboxylase, all components of photosynthesis. While the promoter regions are known for many of these genes, the transcriptional factors that bind to these nucleic acid regions are generally unknown. Furthermore, the signal transduction pathways connecting Pfr to these transcriptional factors are largely unknown. These matters have been recently reviewed in Tobin, E. M. and Kehoe D. M. "Phytochrome regulated gene expression," *Seminars in Cell Biology* 5: 335–46 (1994) to which the reader is directed for more detailed information.

SUMMARY OF THE INVENTION

The present invention involves the isolation and characterization of the first discovered phytochrome-regulated transcriptional factor, a protein designated CCA1 which binds to the promoter region of a chlorophyll binding protein gene (Lhcb1*3) of Arabidopsis. The Lhcb1*3 gene of Arabidopsis is known to be regulated by phytochrome in etiolated seedlings where a brief illumination by red light results in a large increase in the level of mRNA from this gene. Karlin-Neumann, G. A., Sun, L., and Tobin, E. M. *Plant Physiol.* 88:1323–31 (1988). A DNA binding activity, designated CA-1, that interacts with the promoter region of Lhcb1*3 was discovered in cellular extracts. Sun, L., Doxsee, R. A., Harel, E., and Tobin, E. M., *Plant Cell* 5: 109–21 (1993) (Sun et al., 1993). The promoter region to which CA-1 binds has been shown to be necessary for normal phytochrome regulation of the Lhcb1*3 gene. Kenigsbuch, D. and Tobin, E. M. *Plant Physiol.* 108:1023–27 (1995). Modification of the expression of CCA1 using techniques of genetic engineering results in unexpected changes in the timing of plant flowering.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1 gives sequences of the A2 fragment of the Lhcb1*3 promoter and of DNA fragments used in EMSA analysis along with indications of nucleotide modifications that reduce CCA1 binding; in the probe sequences (WT1, m1, m2, m3, m4, and WT2) dashes indicate those nucleotides that are identical to the A2 probe while dots denote gaps introduced to optimize the alignment of conserved sequence elements;

FIG. 2 shows the complete nucleic acid sequence of CCA 1, the genomic clone corresponding to the CCA1 cDNA along with the deduced amino acid sequence of the coding portions of the gene;

FIG. 3 shows the predicted amino acid sequence of CCA1 from amino acid residue 24 to 75 compared to the repeat sequences of various Myb proteins from animals, plants, and yeast;

DETAILED DESCRIPTION OF THE PREFERRED EMBODIMENTS

Figure 4:
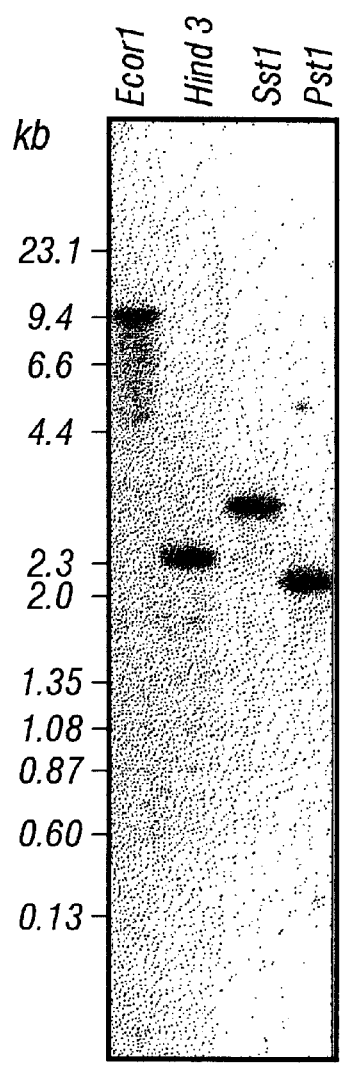
FIG. 4 shows results of low-stringency hybridization of Arabidopsis DNA with a CCA1 probe.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide the nucleic acid sequence, amino acid sequence and cloned protein of a phytoclrome-regulated transcription factor that shows unexpected effects on development and flowering of plants.

Plant Materials and Growth Conditions

Arabidopsis thaliana ecotype Columbia was used in all experiments except for ecotype Nossen (No-O) which was used in transformation experiments with the antisense CCA1_constructs. The medium used for plant growth (MS2S medium) contained 1X MS salts (GIBCO BRL), 0.05% Mes, pH 5.7, 0.8% Phytagar (GIBCO BRL) and 2% sucrose. Light-grown plants were maintained at 24° C. in a growth chamber with light intensity of 150 µE m$^{-2}$ sec$^{-1}$ Growth and light treatments of etiolated seedlings for phytochrome experiments were as described previously (Brusslan, J. A., and Tobin, E. M., *Proc. Natl. Acad. Sci. USA* 89:7791–95 (1992)). White onions used in nuclear localization experiments were purchased from a local supermarket.

Isolation and Sequence Characterization of CCA1 cDNA and Genomic Clones

Poly(A) RNA was isolated from leaves of Arabidopsis grown for 3 weeks on soil in continuous white light. A directional cDNA expression library was constructed in λgt22A using the SuperScript Lambda system (Bethesda Research Laboratory, Bethesda, Md.). The library was screened essentially as described by Singh, H., Clerc, R. G., and LeBowitz, J. H.,. *BioTechniques* 7:252–61 (1989), except that NEB buffer (25 mM Hepes-NaOH, pH 7.2, 40 mM KCl, 0.1 mM EDTA, 5 mM β-mercaptoethanol, 10% glycerol, Sun et al. 1993) was used as the binding buffer, and the washing solution was supplemented with 0.25% non-fat milk and 0.1% Triton X-100.

An Arabidopsis λ cDNA expression library was screened with the radiolabeled A2 fragment of the Lhcb1*3 promoter because this fragment had been previously shown to interfere with CA-1 binding activity in plant extracts. Approximately 640,000 unamplified recombinant phage plaques were screened in the first round using double-stranded A2 DNA probe (A2, FIG. 1). The positive plaques from the initial screening were rescreened using both the A2 probe and a mutant probe (m1 probe, FIG. 1) that is known to poorly bind to the CA-1 activity (Sun et al. 1993). Two phage clones (clones 21 and 24) that bound only to the A2 and not to the m1 probe were isolated as individual plaques. The cDNA inserts were subcloned into the SalI and NotI restriction sites of pGEM11Zf(−)(Promega, Madison, Wis.). Sequence analysis showed that the two clones overlapped by 470 nucleotides and were partial cDNAs derived from the same mRNA. Clone 24 included a polyadenylated tail of 15 bases and, therefore, encompassed the entire 3' region of the mRNA. The 5' end of the mRNA was determined by primer extension analysis as described by Ausubel, F. M., Brent, R., Kingston, R. E., Moore, D. D., Seidman, J. G., Smith, J. A., and Struhl, K., eds., Current Protocols in Molecular Biology (New York: Greene Publishing Associates and Wiley-Interscience) (1987). The sequence of the oligonucleotide primer corresponded to nucleotides +42 to +22 of CCA1 cDNA clone 21. Fifty fmoles of $^{32}$P-labeled primer was annealed to 45 μg of total RNA. The primer was extended using 9.5 units of Avian Myeloblastosis Virus (AMV) reverse transcriptase (Promega) at 37° C. for 1 hr. Dideoxy sequencing reactions were performed using the same $^{32}$P-labeled oligonucleotide primer and CCA1 clone 21 plasmid DNA. This demonstrated that clone 21 included the complete 5' region of the transcript. A full-length cDNA clone, designated clone 25, was constructed by joining the 5' and 3' fragments of clones 21 and 24, respectively, at the unique PstI site in the overlapping region. The 5' end of the cDNA clone 24 was removed as a SalI-PstI fragment and replaced with that of clone 21. Sequencing the region spanning the PstI junction of clone 25 confirmed the reconstitution of wild-type sequence. The sequence of clone 25 is presented as SEQ ID NO:3

A genomic clone corresponding to the CCA1 cDNA was isolated by screening a genomic library of *Arabidopsis thaliana* ecotype Columbia in λGEM11 (Promega, Madison, Wis.), using the SstI-NotI fragment of CCA1 cDNA clone 24 (corresponding to nucleotides 950–2254 of the full-length cDNA). The sequences of the CCA1 cDNA and overlapping fragments of the genomic clone were determined by the dideoxy chain termination method using a Sequenase kit (United States Biochemicals, Cleveland, Ohio) and double-stranded plasmid DNA. Both strands of the cDNA and genomic DNA were completely sequenced.

The sequence of complete gene is shown in FIG. 2 (also SEQ ID NO:1) along with the predicted amino acid sequence for the CCA1 protein. The gene sequence includes seven introns (the first in the 5' noncoding region from nucleotide 190 to 273; the others from nucleotides 361 to 438, 551–638, 701–1179, 1375–1461, 1636–1718, and 2601–2670), 237 nucleotides of 5' untranslated sequence, and 193 nucleotides of 3' untranslated sequence. The 1824-nucleotide open reading frame (ORF) encodes a protein of 608 amino acids with a calculated molecular weight of 66,970 and an isoelectric point of 5.6. An ORF of 24 nucleotides is present in the 5' untranslated region of the transcript and is in phase with the main ORF. Such OAFS have been shown in several cases to be involved in translational regulation of gene expression (Lamer, S., Maddaloni, M., Motto, M., Salamini, F., and Thompson, R. D., *Plant Cell* 5:65–73 (1993); Hinnebusch, A. G., *Trends in Biochem.Sci.* 19:409–14 (1994)), and have also been found in other plant transcription factor genes (Singh, K., Dennis, E. S., Ellis, J. G., Llewellyn, D. J., Tokuhisa, J. G., Wahleithner, J. A., and Peacock, W. J., *Plant Cell* 2:891–903 (1990); Ruberti, I., Sessa, G., Lucchetti, S., and Morelli, G., *EMBO J.* 10:1787–91 (1991); Carabelli, M., Sessa, G., Baima, S., Morelli, G., and Ruberti, I., *Plant J.* 4:469–79 (1993); Lohmer et al., 1993).

Sequence Analysis and Data Base Searching

The protein and DNA sequences were analyzed using the MacVector software (IBI, New Haven, Conn.) and the Genetics Computer Group (Madison, Wis.) software package. The GenBank data base was searched with the amino acid sequence of CCA1 by using the BLAST (Altschul, S. F., Gish, W., Miller, W., Myers, E. W., and Lipman, D. J., *J. Mol. Biol.* 215:403–10 (1990)) and FASTA programs (Pearson, W. R. and Lipman, D. J. *Proc. Natl. Acad. Sci. USA* 85:2444–48 (1988)) on the National Center for Biotechnology Information (NCBI) on-line service. Sequence alignment was assembled manually based on the results of data base searches. Genomic sequences of light-harvesting complex apoprotein (Lhc) genes and small subunit of ribulose bisphosphate carboxylase/oxygenase (rbcS) genes were retrieved from the Genbank data base using text search on the NCBI world wide web site. The presence of AATCT sequences in the promoter regions of the genes was detected using the FASTA program and further analyzed visually.

The predicted amino acid sequence of the CCA1 protein has a basic region at the N terminus (K-13 to K-107). Within this region is a sequence similar to the repeat sequence highly conserved in Myb-related proteins. FIG. 3 shows the predicted amino acid sequence of CCA1 from amino acid residue 23 to 75 compared to the repeat sequences of various Myb proteins from animals, plants, and yeast. Within this sequence, there is a limited amino acid identity (16 of 52; 31%) and substantial similarity (29 of 52; 56%) when compared to the third repeat of human c-Myb. The sequence identity includes two of the three conserved tryptophans present in most Myb proteins. The conserved residues also include seven of the 11 residues that are known to be important for forming the hydrophobic core and maintaining the three-dimensional structure of the Myb repeat, which forms a helix-turn-helix structure (Ogata, K., Hojo, H., Aimoto, S., Nakai, T., Nakamura, H., Sarai, A., Ishii, S., and Nishimura, Y., *Proc. Natl. Acad. Sci. USA* 89:6428–32 (1992)). However, the amino acid residues of human Myb that actually contact the DNA bases are not conserved in CCA1 (N-183 in hMyb, S in CCA1; K-182 versus R; N-186 versus Q; N-179 versus V) (Ogata, K., Morikawa, S., Nakamura, H., Sekikawa, A., Inoue, T., Kanai H., Sarai, A., Ishii, S., and Nishimura, Y., *Cell* 79:639–48 (1994)). In contrast to most other Myb proteins that have been characterized, this region is not repeated in the CCA1 protein. No other significant homology to any protein in the data base was found.

DNA and RNA Gel Blot Analyses

Genomic DNA isolation and DNA gel blotting were performed as described by Brusslan et al. (1993). Membranes were hybridized with $^{32}$P-labeled CCA1 cDNA fragments under high stringency conditions (final washes were at 65° C. in 0.1% SSC, [1X SSC is 0.15 M NaCl, 0.015 M sodium citrate] 0.1% SDS) and then stripped and reprobed under low-stringency conditions (hybridization at 32° C. in buffer containing 50% formamide, 0.25 M NaHPO$_4$, pH 7.2, 0.75 M NaCl, 7% [w/v] SDS, and 1 mM EDTA and final washes at 45° C. in 2×SSC, 0.1% SDS). Total RNA was extracted from Arabidopsis seedlings as described by Brusslan and Tobin (1992). Total RNA was separated on a 1% agarose gel containing formaldehyde and blotted onto ZetaProbe membrane (Bio-Rad, Richmond, Calif.) following the manufacturer's instructions. RNA probes were synthesized by in vitro transcription using linearized plasmid DNA. CCA1 RNA probe was synthesized from CCA1 clone 24. To make the ubq10 RNA probe, a fragment of the 3' untranslated region of the ubq10 gene (Callis, J., Carpenter, T., Sun, S. W., and Vierstra, R. D., Genetics 139:921–39 (1995)) was amplified by polymerase chain reaction (PCR) using the primers:

5'-CTGTTATGCTTAAGAAGTTCAATGT-3' SEQ ID NO:4 and
5'-CCACCCTCGAGTAGAACACTTATTCAT-3' SEQ ID NO:5

The amplified fragment was digested with HinduII and XhoI and cloned into pGEM-11Zf(-). This plasmid DNA was digested with HindIII and used as template for synthesis of ubq10 RNA probe. The Lhcb1*3 RNA probe was made as described by Brusslan and Tobin (1992). The membrane blot was hybridized overnight with the RNA probes in buffer containing 50% formamide, 0.3 M NaCl, 0.05 M NaHPO$_4$, pH 6.5, 1 mM EDTA, 1% SDS, 0.1% Ficoll (type 400), 0.1% polyvinylpyrrolidone, 0.1% BSA, 0.5 mg/mL yeast tRNA and 0.5 mg/mL herring sperm DNA. Hybridization of Lhcb1*3 ubq10 and CCA1 probes was performed at 55° C., 52° C. and 58° C., respectively. Final washes were performed at 65° C. in 0.1×SSC, 0.1% SDS. After hybridization with Lhcb1*3 and ubq10 probes, the blot was stripped by boiling in 0.1×SSC, 0.1% SDS, then hybridized with the CCA1 probe. The blots were imaged and quantified using a PhosphorImager (Molecular Dynamics, Sunnyvale, Calif.). The measurement of the signal for each probe was adjusted for the uridine content of the probe and the exposure time, and the Lhcb1*3 and CCA1 signals were normalized to the ubq10 signal.

We tested whether CCA1 is a member of a gene family in Arabidopsis by genomic DNA gel blot analysis. The results of low-stringency hybridization of Arabidopsis DNA with a CCA1 probe are shown in FIG. 4. There was a single band of hybridization in the lanes that were digested with EcoRI, SstI, and PstI, which have no cleavage site in the probe fragment. There were two bands in the lane that was digested with HindIII, which has a cleavage site in the probe 188 bp from one end. An identical pattern was seen when the blot was hybridized with the same probe under the high-stringency conditions. The DNA gel blots were also hybridized under both low- and high-stringency conditions with a probe consisting of nucleotides 267–949 of the CCA1 cDNA, which includes the region of similarity to the Myb repeat. This probe gave no evidence for any additional closely related sequences. We conclude that although the CCA1 gene includes a small region with amino acid sequence homology to the Myb repeat, there are no genes that are closely related to CCA1 in the Arabidopsis genome.

Partial purification of Arabidopsis CA-i protein, A2 probe labeling, and the electrophoretic mobility shift assays (EMSAs) were carried out as described by Sun et al. (1993). Competitor DNA fragments were prepared by annealing synthetic oligonucleotides. Competition EMSA experiments were performed by adding partially purified plant CA-1 protein or affinity-purified CCA1 polypeptide expressed from pXCA-24 in E. coli to the DNA binding reaction mixture containing A2 probe and specified amounts of competitor DNA fragments. The dried gels were imaged and quantified using a PhosphorImager.

The fact that the two cDNA clones isolated in the initial filter-binding screening each contained the sequence similar to the Myb repeat suggested that this region was necessary for DNA binding. We tested this possibility and further characterized the CCA1 protein by expressing the polypeptides encoded by various fragments of the CCA1 cDNA. The CCA1 cDNA clones were fused to the coding sequence for glutathione 5-transferase (GST) and used to produce the polypeptides in Escherichia coli. These constructs are diagrammed in FIG. 5. The polypeptides produced were tested for their ability to bind to the A2 fragment of the Lhcb1*3 promoter by electrophoretic gel mobility shift assays (EMSA). The polypeptides corresponding to the pXCA-23 and pXCA-24 constructs were produced as isopropyl β-d-thiogalactopyranoside (IPTG)-inducible GST-fusion proteins, and were also tested as purified proteins after cleavage from GST. Those corresponding to the cDNA clones CCA 1–21 and CCA 1–25 (pXCA-21 and pXCA-25, respectively) contained stop codons in the 5' untranslated region of the cDNA and, thus, were not produced as fusion proteins. FIG. 6 shows an EMSA using either E. coli extracts (lanes 1 to 10, 15 and 16) or with purified proteins before (lanes 11 and 13) and after (lanes 12 and 14) cleavage from GST. DNA binding activities induced by IPTG were observed for proteins produced from constructs pXCA-21, pXCA-24, and pXCA-25, but binding activity could not be detected for the protein produced from construct pXCA-23, which lacked the N-terminal 82 amino acids. In conjunction with the finding that the N-terminal 11 amino acids are not necessary for binding (construct pXCA-24), these experiments demonstrate that the sequence containing amino acid residues 11–82 of CCA1, which includes the region with similarity to the Myb DNA binding domain (amino acids 24–75)., is essential for the DNA binding activity of the CCA1 protein. Therefore, homologous CCA1 proteins from other plant species will share this highly conserved binding domain most likely with 85% or higher homology. The asterisk in the figure marks a nonspecific DNA binding activity. The arrow and triangles denote the positions of the major protein-DNA complexes formed by the GST-CCA1 fusion protein and the non-fusion CCA1 polypeptides, respectively. Lanes 15 and 16 are longer exposures of lanes 5 and 6.

Protein Expression in Escherichia coli and Purification of GST-CCA1 Proteins

Figure 5:
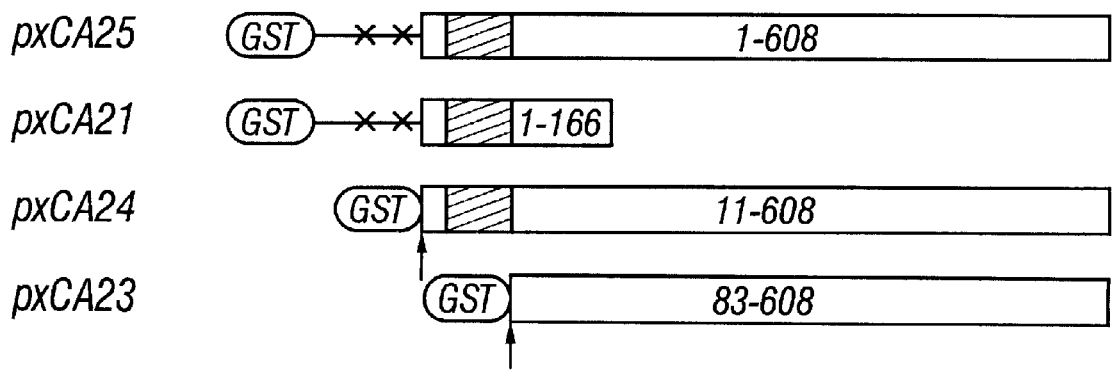
FIG. 5 shows diagrams of the constructs used for expression of CCA1 polypeptides in *E. coli;*
Figure 6:
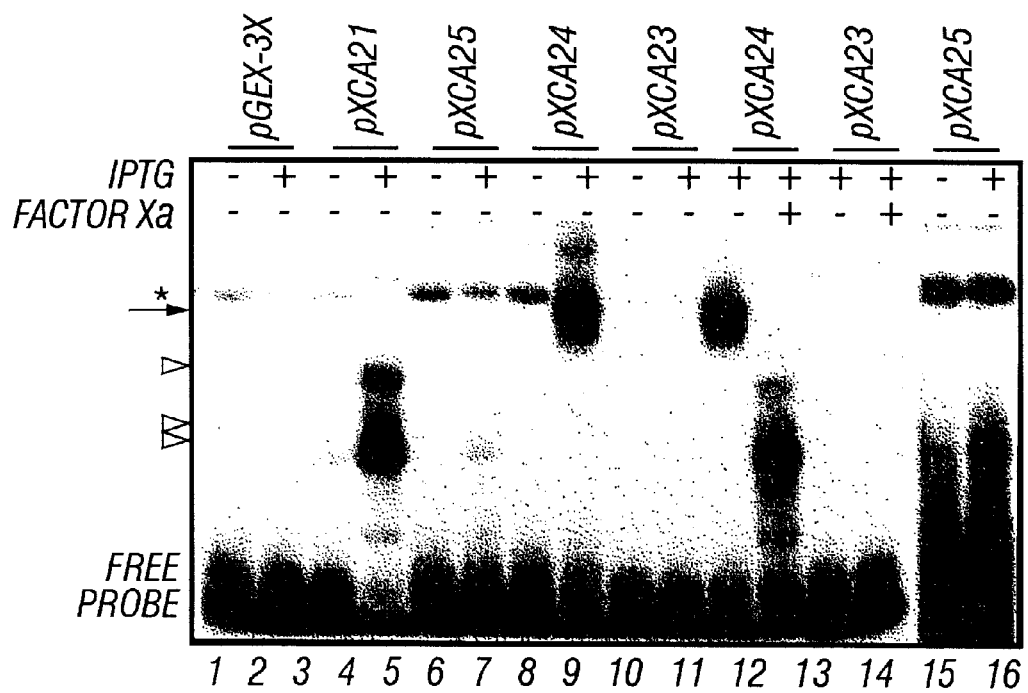
FIG. 6 shows EMSA results for DNA binding activities of polypeptides produced from the constructs of FIG. 5; each reaction included 0.3 ng of $^{32}$P-labeled A2 DNA probe and 1 µg poly(dI-dC); lanes 1–10, 15, and 16 each contain 1 µg of protein for *E. coli* either induced (+) or not induced (−) with IPTG; lanes 11 and 13 each contain 50 ng of purified GST-CCA1 fusion protein (Factor Xa [−]); and lanes 12 and 14 each contain 50 ng of purified CCA1 protein released from the fusion protein by Factor Xa cleavage (Factor Xa[+])

The constructs diagrammed in FIG. 5 were made by cloning the CCA1 cDNA fragments into pGEX-3X (Pharmacia) using polymerase chain reaction (PCR)-aided cloning with the following 5' primers:

5'-GGCCGGGATCCAATTCGTCGACCCACGCG-3' (SEQ ID NO:6) for pXCA-21, pXCA-24, pXCA-25 and
5'-TAAAGGGATCCATATGGGTCAAGCGCTAG-3' (SEQ ID NO:7) for pXCA-23. A 3' primer (5'-ATAGAATTCTCGAGCTTATGCATGCGG-3'(SEQ ID NO:8)) was used for pXCA-21, pXCA-24, pXCA-25 and pXCA-23. The appropriate plasmid DNA (0.5 μg) was amplified for 10 cycles and the PCR products were digested with EcoRI and BamHI. The cDNAs of clones 21, 24, and 25 and the 483 to 2254-nucleotide region were cloned into pGEX-3X yielded pXCA-21, pXCA-24, pXCA-25 and pXCA-23, respectively. Sequencing of the junction region between the glutathione S-transferase (GST) gene and cDNA confirmed the construction of a translational fusion in pXCA-24 and pXCA-23.

The plasmid constructs were transformed into E. coli BL21(DE3). Protein expression, purification of GST-CCA1 fusion proteins using glutathione agarose, and purification of CCA1 polypeptides by cleavage of matrix-bound GST fusion protein with Factor Xa were performed following the procedure of Ausubel et al. (1987). Protein concentrations were determined by the Bradford assay (Bio-Rad, Richmond, Calif.) using BSA as standard.

Phenanthroline-copper Footprinting

The A2 fragment was labeled with $^{32}$P at the 3' end of the sense strand by end filling (Sun et al., 1993). Footprint experiments were carried out as described by Kuwabara, M. D., and Sigman, D. S., Biochemistry 26:7234–38 (1987). The EMSA reactions were scaled up fivefold; $10^6$ cpm of probe and specified amounts of protein and poly(dI-dC) were used in each reaction. After electrophoresis, the gel was treated with phenanthroline-copper, then exposed wet to x-ray film for 40 min. The bands representing free DNA and protein-DNA complexes were excised from the gel. DNA was eluted from the gel slices, recovered by ethanol precipitation, and loaded on an 8% polyacrylamide-urea sequencing gel. The G+A chemical cleavage sequencing reaction was performed as described by Maxam, A. M., and Gilbert, W., Methods Enzymol 65:499–580 (1980).

Partial methylation and depurination of the A2 DNA probe was performed following the procedure of DNA chemical sequencing (Maxam and Gilbert, 1980). Five ng ($10^5$ cpm) of modified DNA probe was incubated with 0.8 $\mu$g of affinity purified CCA1 protein in 50 $\mu$L NEB buffer containing 5 $\mu$g poly(dI-dC) and 10 $\mu$g BSA. The protein-bound and free DNA were separated by filtering the mixture through a nitrocellulose membrane (Ausubel et al., 1987). Free and bound fractions of DNA were recovered, and cleaved with piperidine following the DNA chemical sequencing procedure. An aliquot of probes not incubated with protein was also cleaved with piperidine as a control. Equal amounts of radioactivity from each sample were used on an 8% polyacrylamide-urea sequencing gel.

Figure 7A:
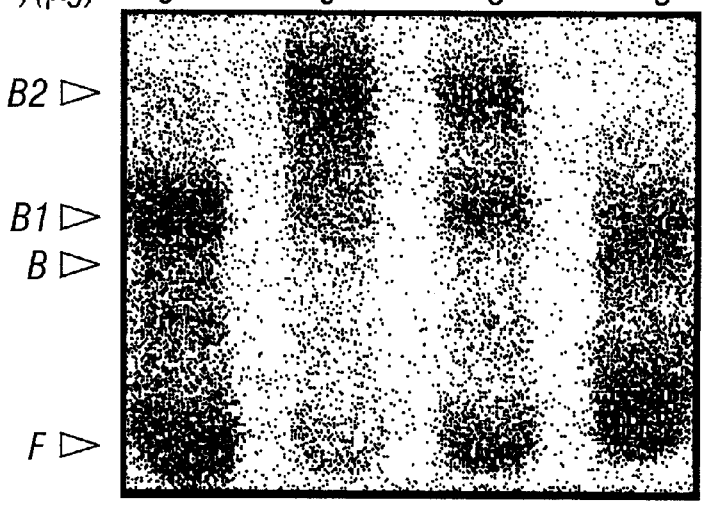
FIG. 7 shows on the left the results of EMSA with the A2 fragment and the amount of proteins and poly (dI-dC) shown above each lane; F, free probe; B, CA-1 protein-DNA complex; B1 and B2, CCA1 protein-DNA complexes; on the right is shown the sequencing gel of the cleaved DNA recovered from the phenanthroline-copper reaction with S lanes representing the G+A chemical sequencing reaction and with the actual sequence of the protected region spelled out.
Figure 7B:
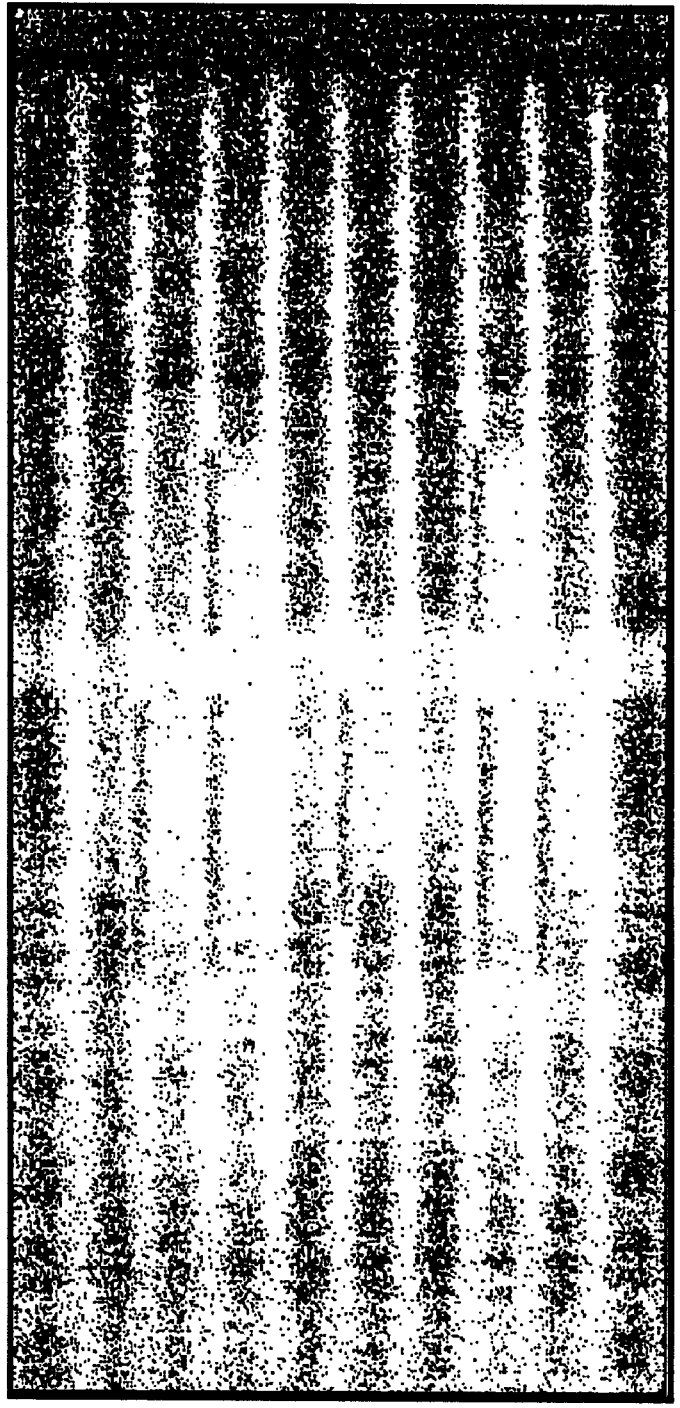

To compare the binding characteristics of the CCA1 protein and CA-1 activity from the plants, we carried out footprint analyses and binding competition experiments using the A2 fragment of Lhcb1*3 promoter as a probe. The results of 1,10-phenanthroline-copper footprinting are shown in FIG. 7. At left is the EMSA that was performed to resolve the free probe and the DNA-protein complexes. Cleaved DNA was recovered from each band after treatment of the gel with phenanthroline-copper and resolved on the sequencing gel shown at right. With increasing amounts of the CCA1 protein purified from E. Coli, complexes (B1 and B2) of different mobilities could be observed. The nucleotides protected from cleavage in each of the complexes can be seen on the sequencing gel on the right. In complex B1, the −92 to −105 region was protected, and in complex B2, regions from −92 to −105 and from −111 to −122 were protected. This result suggests that the two complexes of different mobilities are a result of the presence of two separate binding sites on this fragment, and that the −92 to −105 region is the higher affinity binding site for CCA1. A nearly perfect repeated sequence of AAA$^A$/$_C$AATCTA (SEQ ID NO:9) occurs in each of these footprinted regions.

The CA-1 protein-DNA complex obtained with the plant cell extract (FIG. 7, lane 4) showed protected nucleotides in the region from −94 to −105, and a second experiment confirmed these boundaries, demonstrating that CA-1 (from plant extracts) and CCA1 (from the clone expressed in E. coli) bind to the same region of the Lhcb1*3 promoter.

Figure 8:
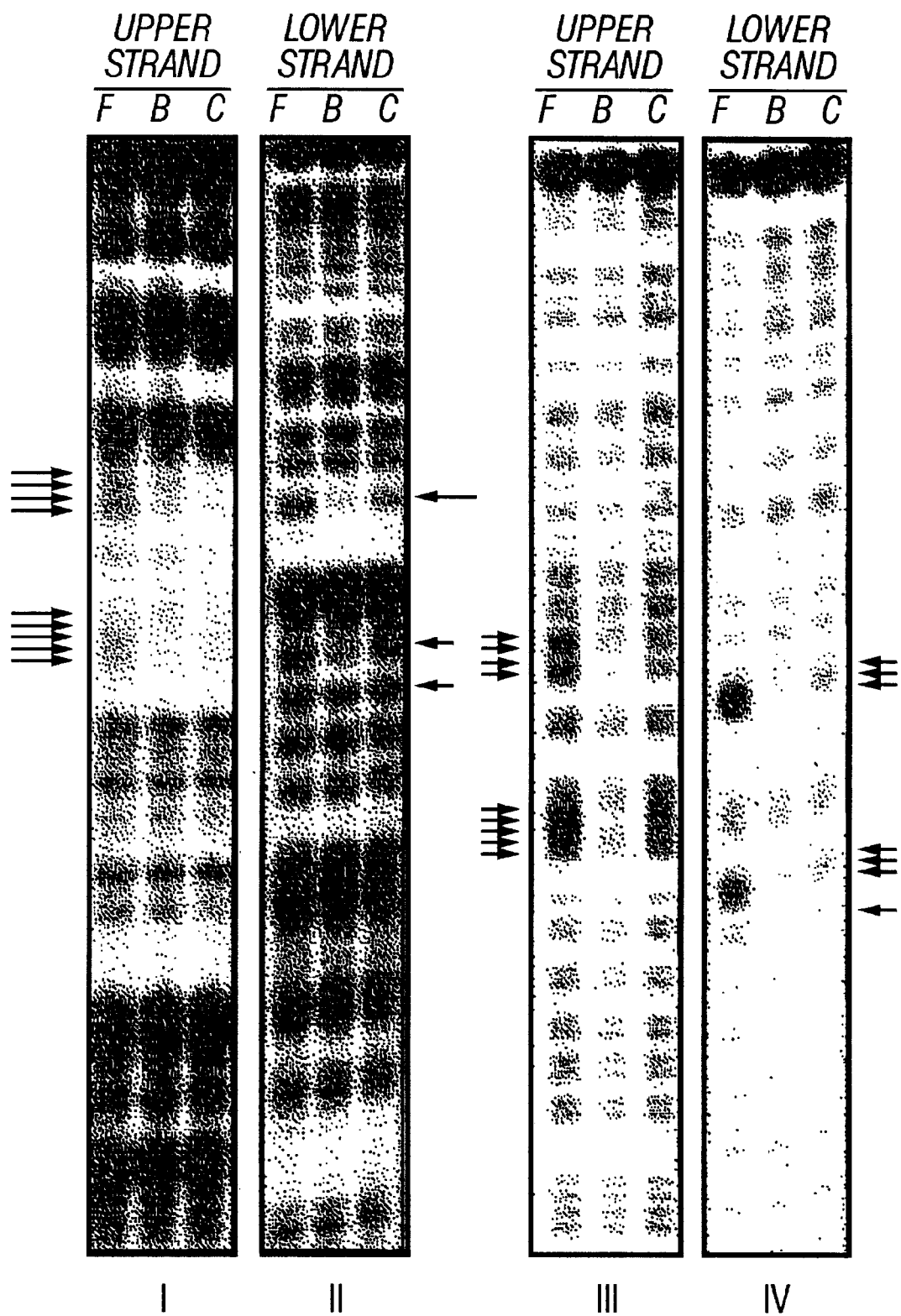
FIG. 8 shows gels of the effects of DNA modification on CCA1 binding where partially methylated (gels I and II) or depurinated (gels III and IV) A2 probe was labeled at the 3' end of either the coding strand (I and III) or the noncoding strand (II and IV) were incubated with CCA1; the free DNA (F), the protein-bound DNA (B) and DNA not incubated with protein (C) were cleaved with piperidine and separated on sequencing gels; arrows mark the positions at which modification of DNA interferes with CCA1-DNA binding.

FIG. 8 show the results of methylation interference and depurination interference experiments performed with the CCA1 protein. The figure shows the interfering nucleotides on sequencing gels, and their position on the A2 fragment of the promoter is shown in FIG. 1, along with the results of footprinting experiments. Interference with the protein-DNA binding by the modification of a base residue is manifested by increased intensity in the lane with the free DNA fraction and reduced intensity in the lane of protein-bound DNA compared to the lane of control DNA that was not incubated with protein. Both methylation and depurination interference assays identified the same nucleotides, and showed that nucleotides within both nearly perfect repeats (AA$^A$/$_C$AATCTA) (SEQ ID NO:10)interact directly with the CCA1 protein. In FIG. 1 thick and thin lines 12 and 14 show the regions protected by CCA1 and CA-1, respectively, in the footprint assay. Asterisks in the figure indicate nucleotides that interfere with CCA1-DNA binding when methylated; boldface indicates the nucleotides that interfere with binding when depurinated.

Figure 9A:
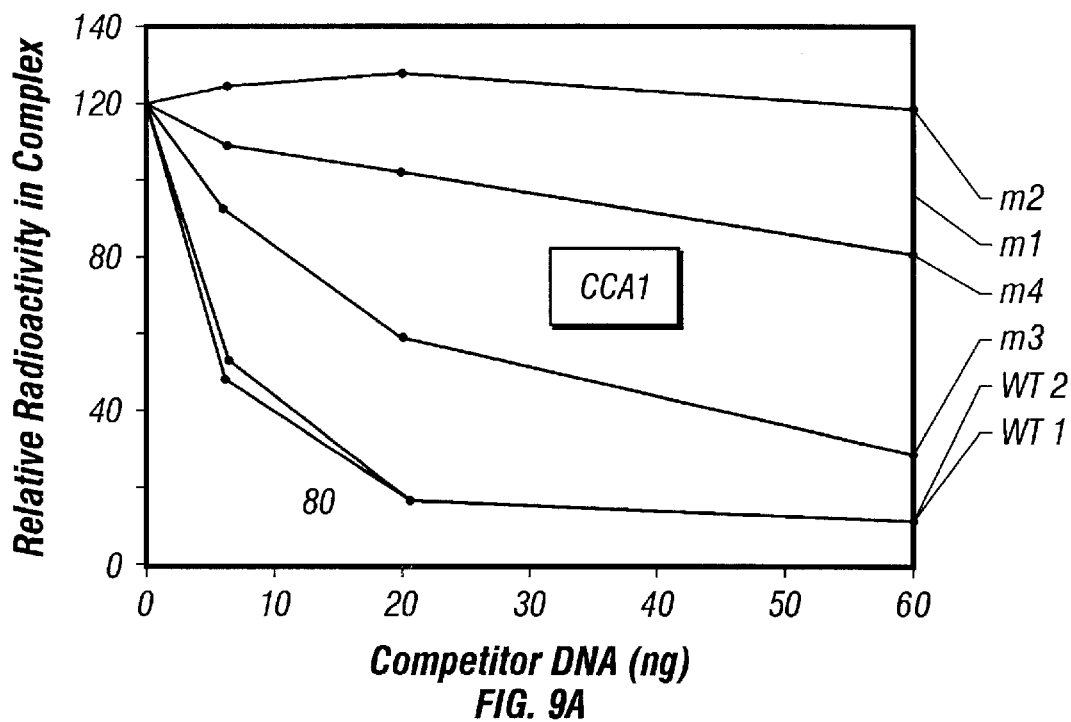
FIG. 9a shows the results of a competition experiment with CCA1.
Figure 9B:
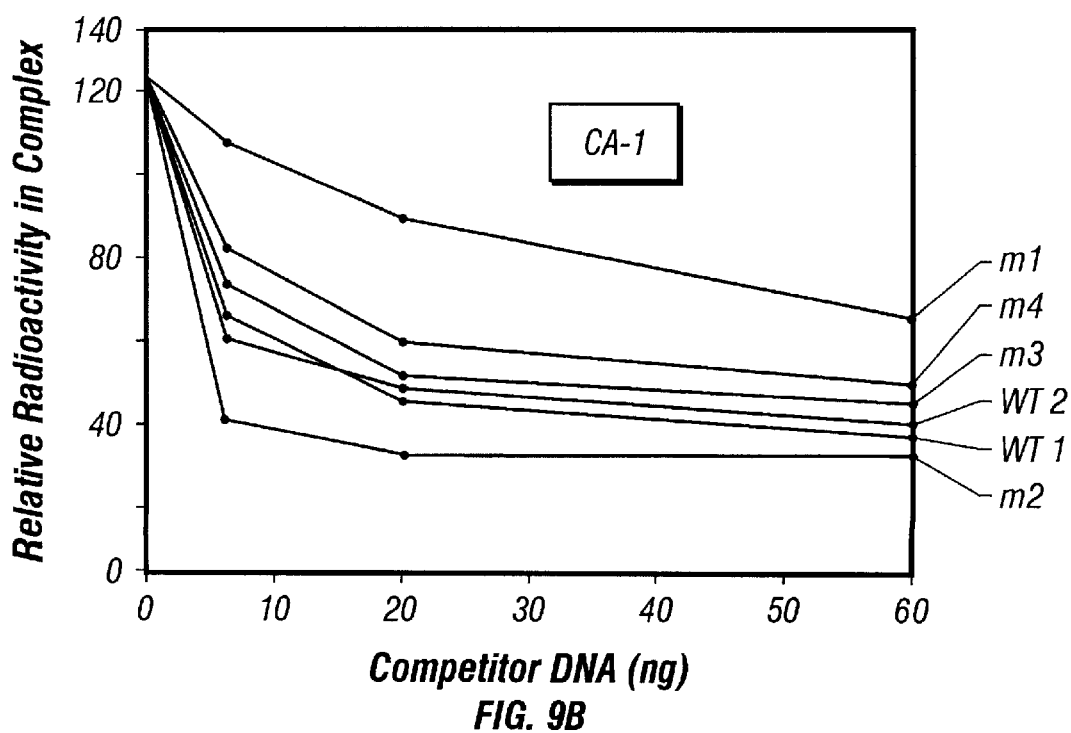
FIG. 9b shows the results of a competition experiment comparable to FIG. 9a but using plant extract CA-1 instead of *E. coli* expressed CCA 1.

FIG. 1 also summarizes the results of the phenanthroline-copper footprinting. We used unlabeled competitor DNAs in the EMSA to compare binding specificities of the CCA1 protein produced in E. coli and the CA-1 activity from the plant extracts. The wild-type and mutant promoter fragments used as competitors are shown at the bottom of FIG. 1. A representative result of such experiments is shown in FIG. 9a for CCA1 and FIG. 9b for CA-1. The binding of the E. coli-produced CCA1 protein to the probe was efficiently competed for by either a fragment of the A2 probe that contained the repeated sequence or by a promoter fragment (WT2) of another closely related Lhcb gene (Lhcb1*1, originally called AB165; Leutwiler, L. S., Meyerowitz, E. M., and Tobin, E. M., Nucl. Acids Res. 14:4051–64 (1986)) that contains one copy of this sequence (AAAAATCT) (SEQ ID NO:11). The m3 fragment, which had altered nucleotides in the downstream repeat region, was a less effective competitor than was the wild-type (WT1); m1, m2, and m4 fragments, which had alterations in both repeats, showed the least competition.

When plant extracts were used, all the fragments showed some degree of competition, which is likely in part to be the result of low amounts of the CA-1 protein in plant extracts. The results are not directly comparable to those with the purified CCA1 protein because the absolute amounts of the specific binding proteins are not known. Nonetheless, it can be seen that the m2 fragment served as a better competitor for CA-1 than did the m1 fragment, whereas the opposite was found with CCA1. Even more striking are the contrasting results with the m4 competitor DNA. This fragment, in which the C residues of both TCT motifs in the two repeats were changed, was even more effective than was the wild type in competing for the CA-1 activity, whereas it was not a particularly good competitor for CCA1. Thus, although both activities interact with the AAAAATCT (SEQ ID NO:11)sequence, there are differences in the importance of individual nucleotides in this sequence for the binding of CA-1 and CCA1.

The CCA1 protein interacted with two closely spaced binding sites with nearly perfect 10-bp repeated sequences (AAA$^A$/$^C$AATCTA)(SEQ ID NO:9)in the Lhcb1*3 promoter. Previous results (Sun et al., 1993) and the results of the phenanthroline-copper footprinting (FIG. 7) show that the CA-1 activity could protect the same nucleic acid sequence as CCA1. There are, however, some differences in the relative importance of specific nucleotides for the binding of the two activities. The binding of CCA1 was more affected by alteration in the TCT sequence than by alterations in the AAAAA, whereas the opposite was observed with the plant extract activity (cf. m3 and m4, FIG. 9). It is possible that the differences observed are due to differences in modifications of the protein in E. coli and plants or that the CA-1 activity in the plant extracts might be associated with an additional protein or proteins which alter the binding characteristics. It is also possible that CA-1 and CCA1 are actually the products of two different genes, or the result of alternative splicing, in which case they may compete for the same binding sites.

Nuclear Localization

Onion epidermal peels were transformed by biolistic transformation and analyzed for GUS activity, and nuclei localization was as described in Varagona, M. J., Schmidt, R. J., and Raikhel, N. V., Plant Cell 4:1213–27 (1992). Histochemical staining was visualized using a Zeiss Axiophot microscope and photographed using Kodak Ektachrome (Elite Series) ASA 400 film.

Transient expression assay in onion epidermal cells tested whether the product of the CCA1 gene was localized to nuclei, as would be expected for a transcription factor. The uidA gene, which encodes, β-glucuronidase (GUS), was fused in frame to the coding sequence of CCA1 so that GUS activity could be used to localize the compartmentation of the CCA1 protein. An XbaI site and a BamHI site were introduced into CCA1 by PCR amplification of cDNA clone 25 using the 5' primer(SEQ ID NO:12)

(5'-GAAGTTGTCTAGAGGAGCTAAGTG-3') and 3'primer (5'-ATGTGGATCCTTGAGTTTCCAACCGC-3')(SEQ ID NO:13)(mismatches are underlined). The resulting PCR product was digested with XbaI and BamHI and inserted in pBI221 (Clontech, Palo Alto, Calif.), yielding p35S-CCA1-GUS. This construct contains CCA1__ coding sequence as a 1828-bp XbaI-BamHI fragment inserted between the cauliflower mosaic virus 35S promoter and the uidA gene. pMF::GUS and pMF::B::GUS were obtained from N. Raikhel (Michigan State University, East Lansing, Mich.); construction of these plasmids is described in Varagona et al. (1992). This transient assay should result in the expression of GUS activity in individual cells into which the DNA is effectively introduced. When a CaMV 35S::uidA construct (pMF::GUS) was used in this assay, GUS activity was detected throughout the cytoplasm. When a construct (pMF::B::GUS) with the opaque2 gene, which encodes a well characterized transcription factor from maize, fused to the uidA gene was used, GUS activity was detected specifically in nuclei. Similarly, specific nuclear localization was found for the CCA1-GUS (p35S-CCA1-GUS) fusion protein. These results show that the CCA1 protein is targeted to nuclei and are consistent with the function of the CCA1 protein as a transcription factor.

Plant Transformation Antisense

Figure 10:
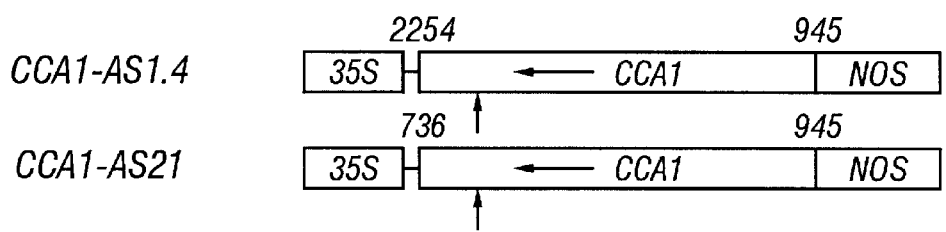
FIG. 10 shows diagrams of constructs for expression of antisense CCA1 in transgenic plants; 35S is the promoter of the cauliflower mosaic virus; NOS the transcription termination sequence of the nos gene while arrows indicate the sense direction of the CCA 1 gene with nucleotide positions numbered.

It has previously been shown that the promoter region to which the CA-1 activity binds is essential for phytochrome regulation of the Lhcb1*3 gene (Kenigsbuch and Tobin, 1995). Therefore, if the product of the CCA1 gene interacts with this promoter in vivo, it might be expected to affect the phytochrome induction of Lhcb1*3 expression. We addressed this possibility by transforming Arabidopsis with portions of the CCA1 gene in an antisense orientation driven by the constitutive cauliflower mosaic virus 35S promoter (see FIG. 10). The SstI-NotI fragments of CCA1 clones 21 and 24 in pGEM11Zf(-) were cloned into pBluescript KS (Stratagene, La Jolla, Calif.) at the corresponding sites. The resulting plasmids were digested with BamHI and SstI, and the cDNA fragments were cloned into the BamHI and SstI sites of binary vector pBI121 (Clontech), replacing the uidA gene coding sequence. The binary vectors were transformed into Agrobacterium tumefaciens A2260. Arabidopsis ecotype No-O plants were transformed with the above constructs using the Agrobacterium-mediated root transformation procedure described by Valvekens, D., Van Montagu, M., and Van Lijsebetten, M., Proc. Natl. Acad. Sci. USA 85:5536–40 (1988).

Figure 11:
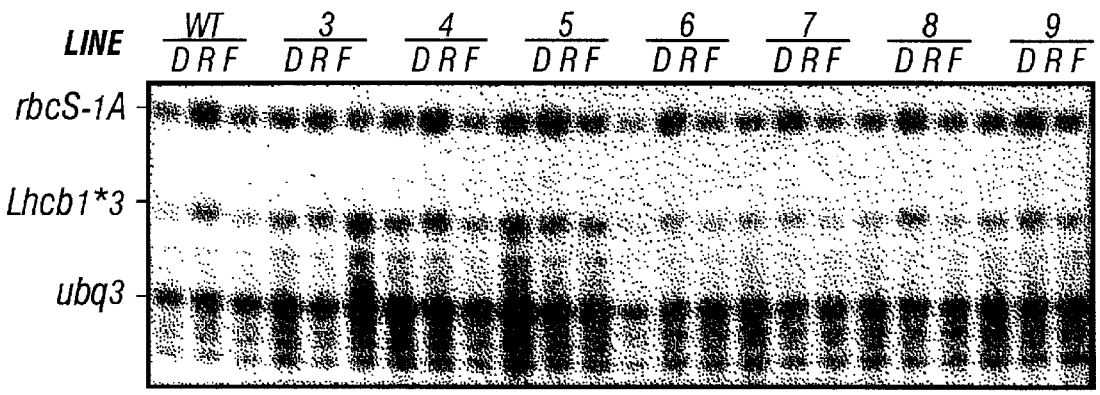
FIG. 11 shows results of RNase protection assays for Lhcb1*3 and rbcS-1A RNA; dark grown seedlings were given no light (D), 2 min R (R) or 2 min R followed by 10 min FR (F) 4 hours before harvesting; WT, wild type; Line 21 transformed with CCA1-AS21 construct; all other lines transformed with CCA 1-AS 1.4; ubq3 gene used as internal control.
Figure 11A:
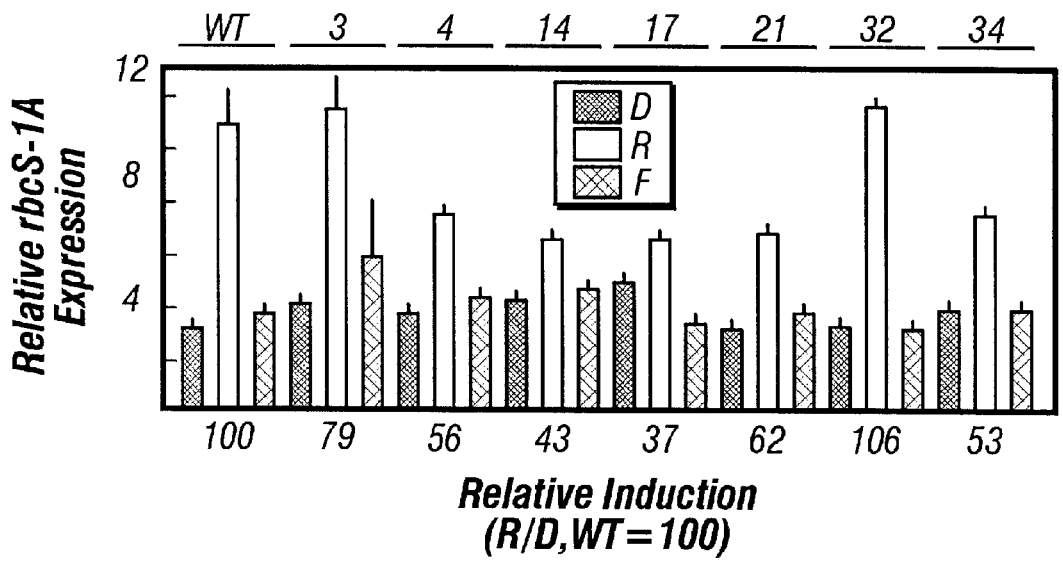
Figure 11B:
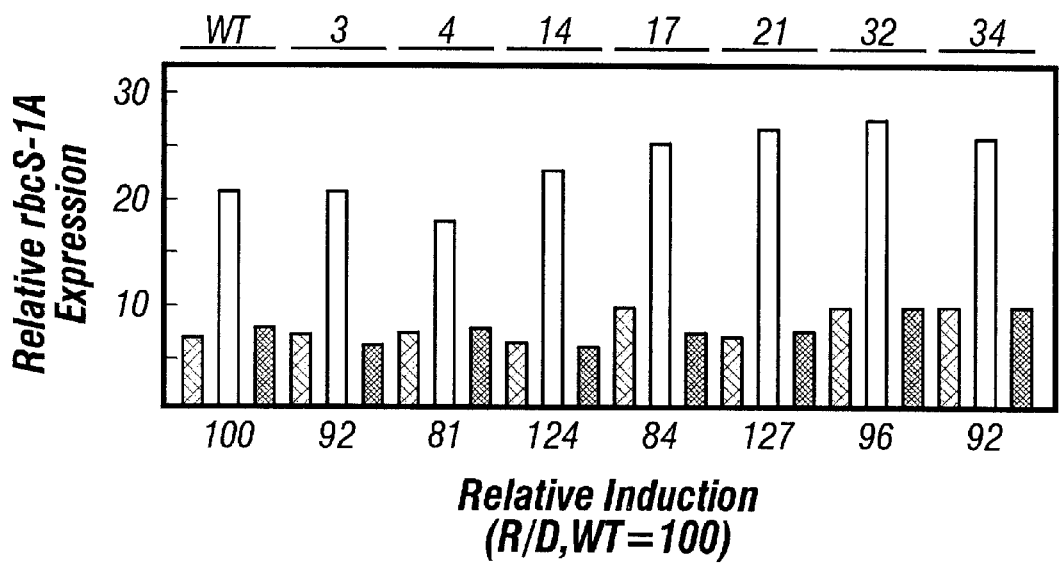

For each independent transgenic line, T2 seeds homozygous for the T-DNA insertion were selected by analysis of the segregation of kanamycin resistance, and seedlings from these homozygous seeds were tested for the phytochrome responsiveness of both the endogenous Lhch1*3 gene and another phytochrome regulated gene, the rbcS-1A gene. FIG. 11 shows that in five of these seven lines, the level of Lhcb1*3 mRNA after the red treatment was substantially lower than that of the wild-type. However, no substantial effect of the antisense construct was seen for rbcS-1A gene expression in the same lines. The mRNA levels for Lhcb1*3 and rbcS-1A were normalized to a ubiquitin RNA (ubq3; cf. Brusslan and Tobin, 1992), and the relative expression levels of these two genes for all the lines and treatments are shown below the autoradiogram. The increase of Lhcb1*3 RNA in response to R was reduced in lines 4, 14, 17, 21, and 34, ranging from 37–53% that of the wild type, but the induction of the rhcS-1A RNA was not comparably affected. The fact that none of the lines we recovered showed strong suppression of CCA1 RNA suggests the possibility that complete loss of function might be highly deleterious. It is also notable that the antisense construct did not affect the mRNA levels in plants that had been given no light treatment or had been given FR following the R treatment. No obvious visible phenotype was apparent in the antisense lines.

We also used the T3 generation of four of the lines to test whether the reduction in Lhcb1*3 RNA correlated with a reduction in levels of CCA1 RNA. In this generation, there was a smaller effect of the antisense construct. It is not unusual for antisense effects to be lost or diminished in subsequent generations. For example, Chamnongpol, S., Willekens, H., Langebartels, C. Van Montagu, M. Inzé, D. And Van Camp, W., Plant J. 10:491–503 (1996) found that seven of eight lines expressing an antisense construct for a catalase gene lost the catalase suppression phenotype in their progeny. The R induction of Lhcb1*3 RNA ranged from 68 to 86% of the wild-type in the T3 seedlings of these four lines, and the levels of CCA1__RNA were 68 to 75% that of the wild-type plants. Although the effect of the antisense constructs was substantially reduced in this generation, the reduction of CCA1 RNA was accompanied by a similar decrease in the induction of Lhcb1*3 RNA by R. Our results demonstrate that the CCA1 protein can have a specific effect on the phytoclhrome induction of expression of the endogenous Lhcb1*3 gene in vivo, and strongly indicate that this protein is a part of the normal transduction pathway for the phytochrome response of this gene.

Plant Transformation Constitutive Expression

Figure 12A:
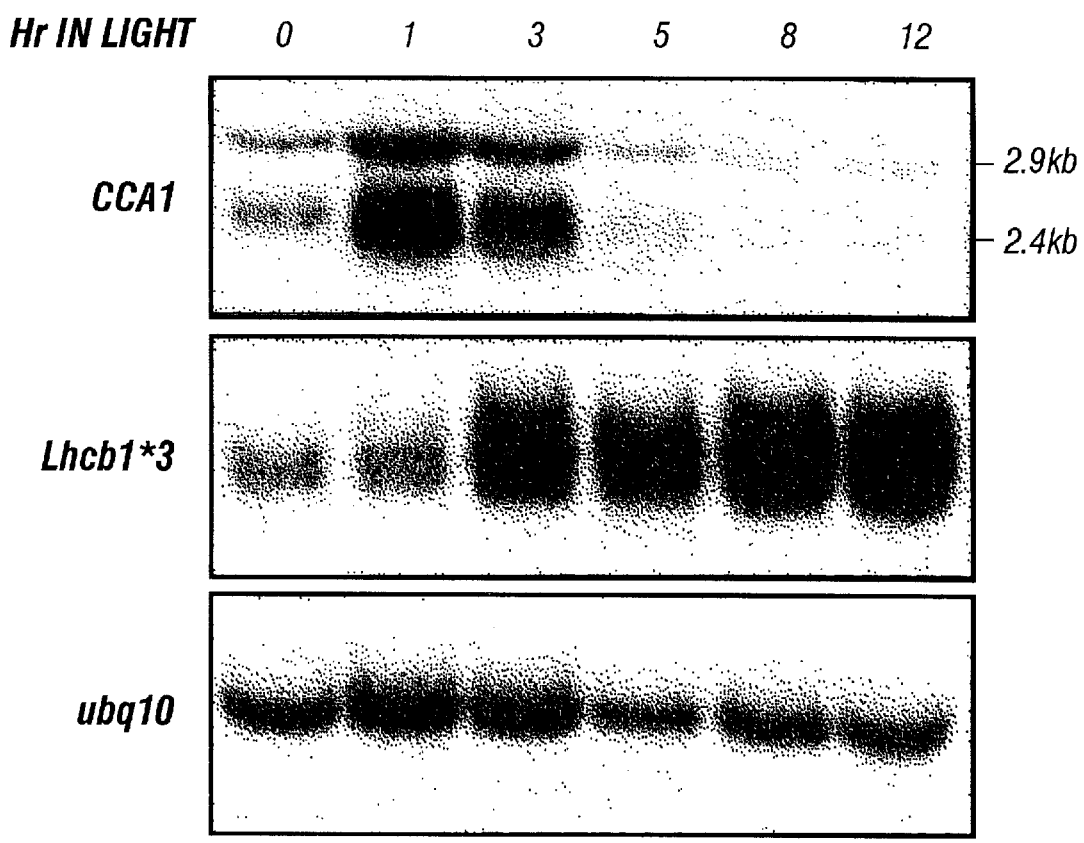
FIG. 12 shows the induction of CCA1 RNA in etiolated seedlings which were grown for six days in the dark and then transferred to continuous light; RNA samples were taken either immediately before the transfer (0) or at the specified time after transfer and analyzed on gel blots.
Figure 12B:
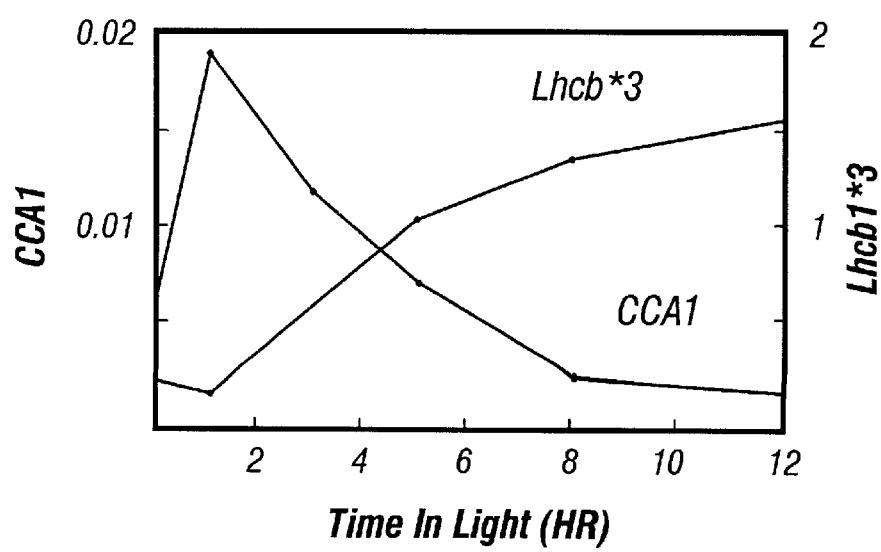

As demonstrated above, CCA1 is a transcription factor that is intimately involved in the phytochrome-induced regulation of Lhcb1*3 and the corresponding light harvesting chlorophyll binding protein. Somewhat paradoxically CCA1 may be itself phytochrome regulated. FIG. 12 shows the time course of production of CCA1 and Lhcb1*3 RNAs when dark-grown seedlings are transferred into light. CCA1 is induced within 1 hr and peaks at before 2 hr, thereafter decaying away. Lhcb1*3 begins to appear following the peak in CCA1 and continues at a high level as long as the plants remain in the light. This transient CCA1 response might suggest involvement of CCA1 in more complex events.

Figure 13A:
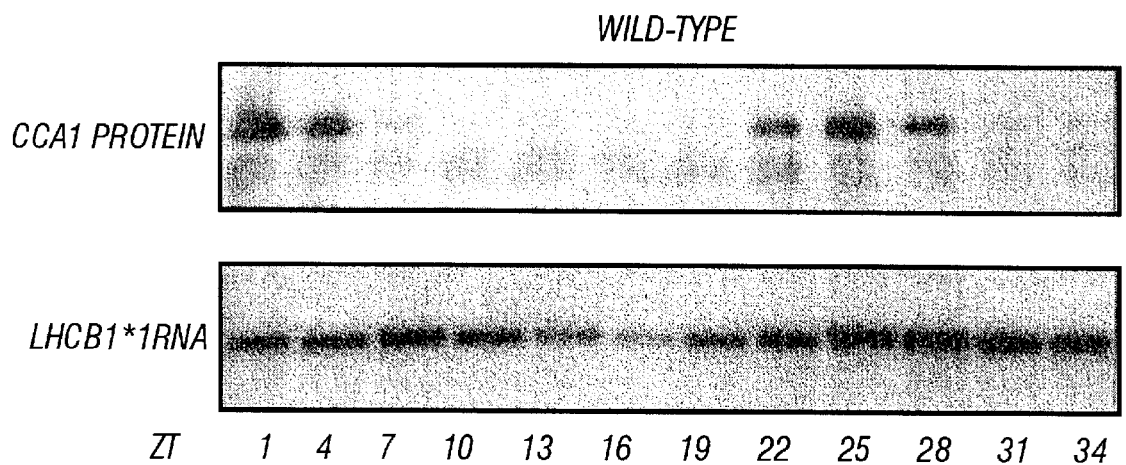
FIG. 13a shows the circadian concentrations of CCA1 protein in a wild type plant along with the concomitant response of Lhcb 1*3 RNA.

One way of exploring the overall effects of the phytochrome control of CCA1 is to remove it from this phytochrome control and ascertain what, if any effects, there are on plant growth and development. This can be achieved by reversing the direction of the CCA1 sequence inserted into the constructs shown in FIG. 10. Now instead of producing an antisense message, the CCA1 gene behind the 35S cauliflower mosaic promoter results in constitutive production of the CCA1 protein. FIG. 13a shows the circadian variations in wild-type expression of CCA1. Here the plants have been grown under a normal light/dark regime and then transferred into continuous light. The endogenous circadian rhythm of CCA1 production continues even under constant light. This rhythm closely matches the original light/dark period as is indicated by the time line. Note that the CCA1 is fully expressed at the start of the light period (ZT 1). This production decays before the end of the light period so that by the start of the dark period (ZT 12) CCA1 production is essentially absent—even though the plants remain under constant illumination. CCA1 production leads the beginning of the next light period (ZT 25) being apparent by ZT 19. This circadian rhythm was originally entrained to light/dark periods but clearly continues in plants kept in constant light. Lhcb1*3 RNA tracks CCA1 but decays more slowly so that its level reaches a minimum during the dark period some hours after minimal CCA1 levels have been reached. This difference in phase between CCA 1 and Lhcb1*3 RNA results from a lag between CCA1 protein synthesis and RNA synthesis and slow turnover of Lhcb1*3 RNA. However, it is possible that this lag is actually part of the "clock" mechanism by which the plant actually maintains it circadian rhythm.

Figure 13B:
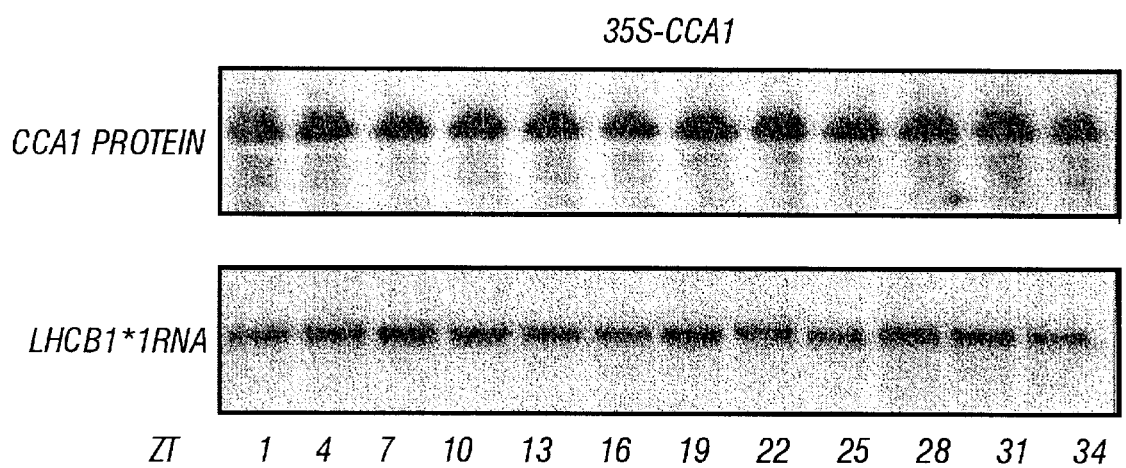
FIG. 13b shows the circadian concentrations of CCA1 protein and Lhcb1*3 RNA in a transgenic plant where CCA1 is constitutively expressed.

FIG. 13b shows that when CCA1 is constitutively expressed in a transgenic plant not only does CCA1 levels remain constant(as expected) but Lhcb1*3 RNA levels also remain constant, thereby damping or obscuring the entire circadian rhythm of Lhcb1*3. In the presence of light the expression pattern of CCA1 now controls the expression of. Lhcb 1*3. However, if CCA 1 is actually part of the "clock" mechanism, overall results may be more profound.

Figure 14:
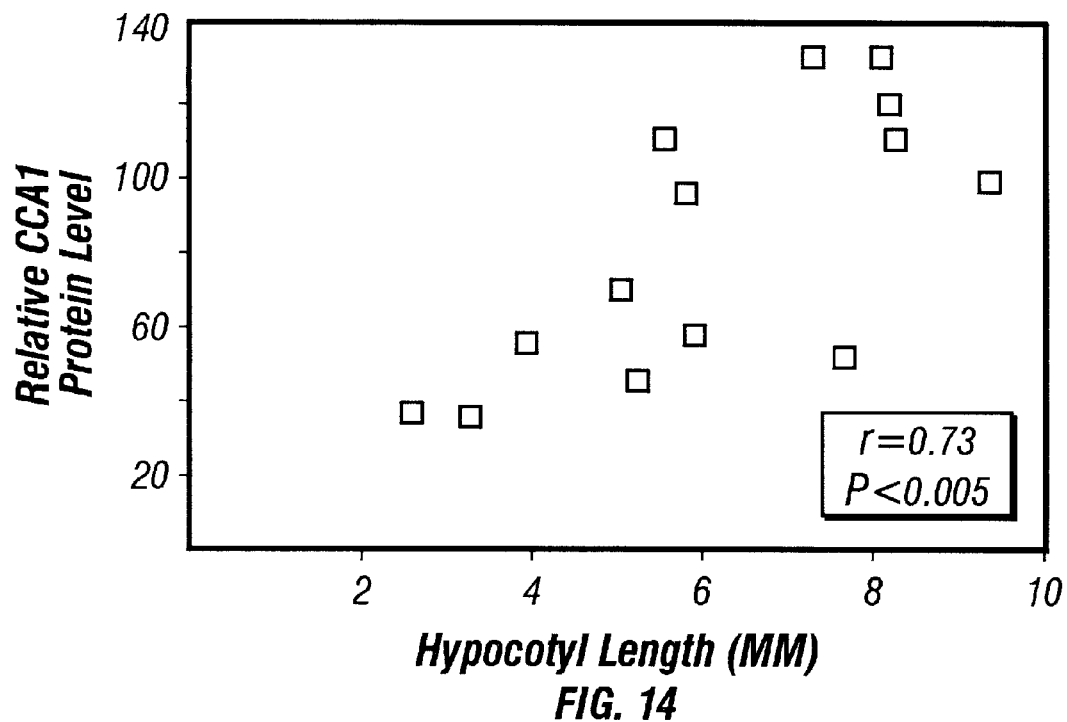
FIG. 14 shows a plot of CCA1 protein level versus hypocotyl length in a number of transgenic plant lines that were transformed with a CCA1 nucleic acid sequence according to the present invention.

The real question, then, is whether this apparent damping of the circadian rhythm affects only the level of Lhcb1*3 transcription or represents a more widespread influence on the "clock" that controls plant development and whether such an effect is exhibited under normal light/dark regimes as opposed to constant illumination. Generally the phenotype of the 35S-CCA1 plants is normal. One of the only detectable morphological effects appears to be a relationship between hypocotyl length measured at six days and CCA1 level in a given plant. CCA1 levels can vary considerably from one transgenic line to another. FIG. 14 shows a regression analysis of hypocotyl length versus CCA1 level for 14 different transgenic lines. There is a strong correlation (r=0.73) between increased hypocotyl length and increased levels of CCA1 indicating that longer hypocotyls results from CCA1 overexpression-certainly not a result expected from a transcription factor that controls Lhcb1*3 RNA. Normally, hypocotyls are shorter in bright light than in dark-grown plants. Perhaps the constitutive CCA1 expression is interfering with the plant's perception of light versus dark. This does suggest that CCA1 effects go beyond Light harvesting chlorophyll binding protein.

Much more exciting and totally unexpected is the effect of CCA1 level on days to flowering of Arabidopsis. Normally the plants are influenced both by day length and by days of growth from seed germination. Under short day conditions the plants will show a relatively prolonged growth phase before they bolt and begin to flower. However, under long day conditions the plants very quickly transit from the vegetative phase to the reproductive phase. That is, if seeds are germinated late in the season (as the days are growing longer) even small seedlings quickly begin to flower completely skipping most of the normal vegetative growth phase. This same behavior is shown by a large number of plants. Most gardeners are well aware of the way that radishes, spinach and lettuce will begin to flower as the sumrner approaches. This behavior is annoying since the palatability of the vegetables is ruined. This behavior is of far greater economic importance with forage crops, in particular pasture grasses such as rye or fescue. The main value of these crops is in the food their vegetative structures provide to domestic animals. When the forage plants begin to flower, their production of vegetative biomass ends and their value as a crop ceases. Until the present invention the only way to deal with this problem was the use of traditional plant breeding methods to select varieties that were slower to flower. This approach has had some little success but the selected varieties could be improved. By a further delay in flowering.

Figure 15:
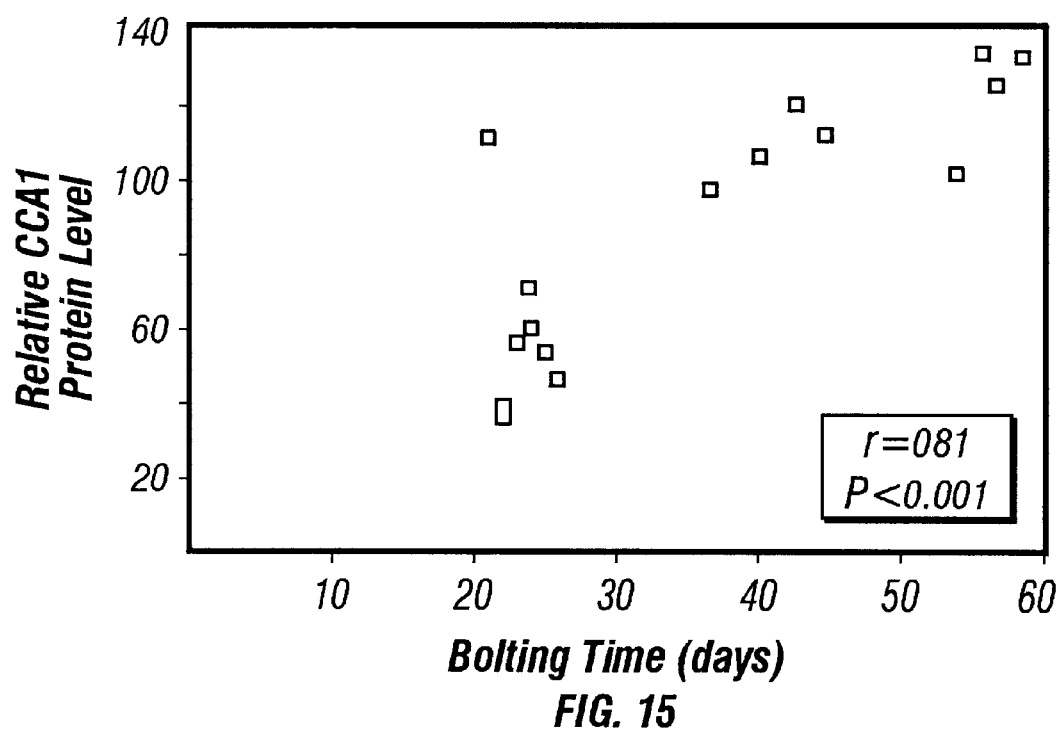
FIG. 15 shows a plot of CCA1 protein level versus bolting time (in days from seed germination) in a number of transgenic plant lines that were transformed with a CCA1 nucleic acid sequence according to the present invention.

FIG. 15 plots the number of days to flowering (bolting) from seed germination for a number of different transformed lines that overexpress CCA1. Just as hypocotyl length was related to CCA1 level in FIG. 14, in FIG. 15 bolting time is highly correlated with CCA1 level (r=0.81). As CCA1 level increases, flowering is delayed so that CCA1 affords the first general method for delaying flowering in plants. This is strong evidence that CCA1 is more than just a transcription factor for regulating Lhcb1*3 RNA. Since altering the level of this factor significantly delays flowering and apparently damps circadian rhythms it seems likely that this factor is part of the "clock" mechanism and is intimately involved in the regulation of a large number of "timing" related aspects of plant development. Since the DNA-binding portion (amino acids 24–75) of CCA1 is highly conserved it is very likely that this protein will be effective in a wide variety of plants and that the method of the present invention will modify flowering in virtually all plants. Conversely, while other species may have homologous CCA1 proteins whose sequences vary from that disclosed herein, the method of using those sequences to modify flowering time is identical to that disclosed and claimed herein. Alteration of plant development by transformation of plants with any nucleic acid sequence that translates to a transcription factor showing significant homology to the key bindino region (amino acids 24–75) of CCA1 is contemplated by the present invention.

Now by constitutively expressing CCA1 it is possible to disrupt the plants built in timing system. With this system disturbed, the plant is much less able to respond to increases in day length as the growing season progresses. This results in a significant increase in vegetative growth and accumulated biomass before a transition to the reproductive state occurs. In the case of forage crops this translates to a dramatic yield increase as a given planting continues to produce biomass for a longer time. In the case of seed crops (e.g. rape seed a relative of Arabidopsis) a delay of flowering can translate to larger plants and a larger seed yield as long as flowering is not delayed too long into the growing season. The first phytochrome-regulated transcription factor provided by the present invention represents the first known way to manipulate plant circadian rhythms and hence flowering through genetic engineering. It seems likely that CCA1 will also serve as the key to unlock other aspects of the phytoclirome-based timing system in plants.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An isolated polynucleotide comprising a member selected from the group consisting of:

(a) a polynucleotide sequence according to SEQ ID NO: 1; and (b) a polynucleotide that is complementary to polynucleotide (a).

2. An isolated polynucleotide comprising a member selected from the group consisting of:

(a) a polynucleotide sequence according to SEQ ID NO:3; and (b) a polynucleotide that is complementary to polynucleotide (a).

3. A method of altering the time of flowering comprising transforming a plant with nucleic acid sequence selected from the group consisting of:

(a) a polynucleotide sequence according to SEQ ID NO:1;

(b) a polynucleotide sequence according to SEQ ID NO:3; and (c) a polynucleotide which hybridizes to polynucleotide (b) under a wash stringency of 0.1×SSC, 0.1% SDS at 65° C. and which functions to produce a CCA1 antisense message.

4. A transgenic plant produced by transforming a plant with a nucleic acid sequence selected from the group consisting of:

(a) a polynucleotide sequence according to SEQ ID NO:1;
(b) a polynucleotide sequence according to SEQ ID NO:3; and
(c) a polynucleotide which hybridizes to polynucleotide (b) under a wash stringency of 0.1×SSC, 0.1% SDS at 65° C. and which functions to produce a CCA1 antisense message.

* * * * *

SEQUENCE LISTING

<160> NUMBER OF SEQ ID NOS: 13

<210> SEQ ID NO 1:
<211> LENGTH: 4344
<212> TYPE: DNA
<213> ORGANISM: Arabadopsis/thalia

<400> SEQUENCE: 1

```
g cagtggttca                                                            11 cttacaagaa cctggtcttc aaaccagaca ggttaaccaa ttctctcttt aactctgtgt       71
ttggttgcat gtaatactga gaatggaaga ctcaaattct cgaggaaatt gtttgttatc      131
tgtttcaggg aggctttgtt tgagaaggtc aagagcacat acaaagacat attagggagc      191
agctgaatca aggaggaag aagaagaaga agagcctttt tgaggccatt catgaattgg       251
aatgaaggat atcaaaagaa tctaacacaa aggccacgtc cttccttcaa tctttccttc      311
ttgtaactaa ataattttca tcctttctct ctctctgtct ctggtctttt ttagctcaaa      371
gtatcatcca tttatgtcaa agtgttgtaa attcctcaag actatatatg agatgttttg      431
tttcattttc caaaatttca aactttgtcc ccatttagtc ttctacccct catgcatggt      491
tagcttagct taatgctgaa ctgttgaata acgatatggg ccttatgcta aaagaacaaa      551
accttatggg tctaaaaaaa ataagcccaa tataaaacta tggcccaaat aagtttaggt      611
ccattagagt gtgagaatag cgcgtgtagt gaaccgcacg agaatgcgcg ttcgattgtt      671
ggtgaagtag tcgtctagat tcccgggtcc actgatgttt ctagtgtatc agacacgtgt      731
cgacaaactg gtgggagaga ttaacgatct taagtaggtc ccactagatc aagatattat      791
aacgaattga cctttttaac ctttcaggta gtcccggaac tcgtggccta gaatacaaag      851
aaggttgtga acaagttgat gttaagatgg acaagaatgt aacttgaaca aaagctgaat      911
catctcttca gccactagta tgttgacata tggcagtttc ttttgtagcc tcgaaataaa      971
taaattaaaa agtttgaggt taaagataat tatagtggct gagatttctc catttccgta     1031
gcttctggtc tcttttcttt gtttcattga tcaaaagcaa atcacttctt cttcttcttc     1091
ttctcgattt cttactgttt tcttatccaa cgaaatctgg aattaaaaat ggaatcttta     1151
tcgaatccaa gctgattttg tttctttcat tgaatcatct ctctaaaggt acttaagatt     1211
gatttattgt catggtcttt cttattgttt gatgaataac ttgacttgat tgttttttgt     1271
tttgtggatt agtggaattt tgtaaagaga agatctgaag ttgtgtagag gagcttagtg     1331 atg gag aca aat tcg tct gga gaa gat ctg gtt att aag gtaaattaac         1380
Met Glu Thr Asn Ser Ser Gly Glu Asp Leu Val Ile Lys
  1               5                  10 taaattttag ggggaagatg attgttttag gtgtcaaaga ttgagaattt taatgaaact     1440 tgatatag act cgg aag cca tat acg ata aca aag caa cgt gaa agg tgg      1490
        Thr Arg Lys Pro Tyr Thr Ile Thr Lys Gln Arg Glu Arg Trp
                15                  20                  25 act gag gaa gaa cat aat aga ttc att gaa gct ttg agg ctt tat ggt       1538
```

-continued

```
Thr Glu Glu His Asn Arg Phe Ile Glu Ala Leu Arg Leu Tyr Gly
        30                  35                  40 aga gca tgg cag aag att gaa g gttgattttt atttcccttt atatgtctta        1590
Arg Ala Trp Gln Lys Ile Glu
        45              50 tttttgtgt tgcagaggt tgtcttcaa actgatttgc ttttttcat ttggacag           1648 aa cat gta gca aca aaa act gct gtc cag ata aga agt cac gct cag       1695
Glu His Val Ala Thr Lys Thr Ala Val Gln Ile Arg Ser His Ala Gln
                55                  60                  65 aaa ttt ttc tcc aag gtaaaatcgg ttaattttga atgatgttc tcatcttcat        1750
Lys Phe Phe Ser Lys
            70 tggcttaatg cttaagactt attgaaagcc aggcaagttt tctgcttctt ttgcttctta     1810 gtcaggagat agatagatta cgttttaga gtttagtaat gagcaataag tcttaaaata      1870 gttggagaaa tgacgagatg taatcgtttt cttttgttta tgcctatatc ttgttaatcc     1930 acaaacatgt acatagattc ttcagaagaa tgttagtttc tttagattct tcagataaac     1990 ttgtgtcttc ttaccgattc tgaggtagtg gcaaaagtgg gctgagtgct agaaattttt    2050 gaatgttcct tgtgataagc catagaggta aaccattttt gatttccag ttctgtcatt     2110 taaacttgtt aggtgtcatt agattttgt tgtttacgt ttgtttagag ggtaacaaaa      2170 ctactctcat ctctctcag gta gag aaa gag gct gaa gct aaa ggt gta gct     2222
                     Val Glu Lys Glu Ala Glu Ala Lys Gly Val Ala
                             75                  80 atg ggt caa gcg cta gac ata gct att cct cct cca cgg cct aag cgt      2270
Met Gly Gln Ala Leu Asp Ile Ala Ile Pro Pro Pro Arg Pro Lys Arg
        85                  90                  95 aaa cca aac aat cct tat cct cga aag acg gga agt gga acg atc ctt      2318
Lys Pro Asn Asn Pro Tyr Pro Arg Lys Thr Gly Ser Gly Thr Ile Leu
    100                 105                 110 atg tca aaa acg ggt gtg aat gat gga aaa gag tcc ctt gga tca gaa      2366
Met Ser Lys Thr Gly Val Asn Asp Gly Lys Glu Ser Leu Gly Ser Glu
115                 120                 125                 130 aaa gtg tcg cat cct gag gtgattttca tggtcatatg gcatctttt gcagtgtgtc   2424
Lys Val Ser His Pro Glu
            135 acattgctcc tcatgttatt aatacagatt gtgtgcttcg tttatag atg gcc aat      2480
                                                    Met Ala Asn gaa gat cga caa caa tca aag cct gaa gag aaa act ctg cag gaa gac      2528
Glu Asp Arg Gln Gln Ser Lys Pro Glu Glu Lys Thr Leu Gln Glu Asp
140                 145                 150                 155 aac tgt tca gat tgt ttc act cat cag tat ctc tct gct gca tcc tcc      2576
Asn Cys Ser Asp Cys Phe Thr His Gln Tyr Leu Ser Ala Ala Ser Ser
                160                 165                 170 atg aat aaa agt tgt ata gag aca tca aac gca agc act ttc cgc gag      2624
Met Asn Lys Ser Cys Ile Glu Thr Ser Asn Ala Ser Thr Phe Arg Glu
        175                 180                 185 ttc ttg cct tca cgg gaa gag gtaaaaaaca atctttcatt gctatttgag         2675
Phe Leu Pro Ser Arg Glu Glu
            190 gttttaagac gattagtact tttcatgaaa ctaaaaccgt gggggaataa cag gga       2731
                                                            Gly
                                                            195 agt cag aat aac agg gta aga aag gag tca aac tca gat ttg aat gca     2779
Ser Gln Asn Asn Arg Val Arg Lys Glu Ser Asn Ser Asp Leu Asn Ala
            200                 205                 210 aaa tct ctg gaa aac ggt aat gag caa gga cct cag act tat ccg atg     2827
```

-continued

```
                Lys Ser Leu Glu Asn Gly Asn Glu Gln Gly Pro Gln Thr Tyr Pro Met
                    215                 220                 225 cat atc cct gtg cta gtg cca ttg ggg agc tca ata aca agt tct cta        2875
His Ile Pro Val Leu Val Pro Leu Gly Ser Ser Ile Thr Ser Ser Leu
        230                 235                 240 tca cat cct cct tca gag cca gat agt cat ccc cac aca gtt gca gga        2923
Ser His Pro Pro Ser Glu Pro Asp Ser His Pro His Thr Val Ala Gly
    245                 250                 255 gat tat cag tcg ttt cct aat cat ata atg tca acc ctt tta caa aca        2971
Asp Tyr Gln Ser Phe Pro Asn His Ile Met Ser Thr Leu Leu Gln Thr
260                 265                 270                 275 ccg gct ctt tat act gcc gca act ttc gcc tca tca ttt tgg cct ccc        3019
Pro Ala Leu Tyr Thr Ala Ala Thr Phe Ala Ser Ser Phe Trp Pro Pro
                280                 285                 290 gat tct agt ggt ggc tca cct gtt cca ggg aac tca cct ccg aat ctg        3067
Asp Ser Ser Gly Gly Ser Pro Val Pro Gly Asn Ser Pro Pro Asn Leu
            295                 300                 305 gct gcc atg gcc gca gcc act gtt gca gct gct agt gct tgg tgg gct        3115
Ala Ala Met Ala Ala Ala Thr Val Ala Ala Ala Ser Ala Trp Trp Ala
        310                 315                 320 gcc aat gga tta tta cct tta tgt gct cct ctt agt tca ggt ggt ttc        3163
Ala Asn Gly Leu Leu Pro Leu Cys Ala Pro Leu Ser Ser Gly Gly Phe
    325                 330                 335 act agt cat cct cca tct act ttt gga cca tca tgt gat gta gag tac        3211
Thr Ser His Pro Pro Ser Thr Phe Gly Pro Ser Cys Asp Val Glu Tyr
340                 345                 350                 355 aca aaa gca agc act tta caa cat ggt tct gtg cag agc cga gag caa        3259
Thr Lys Ala Ser Thr Leu Gln His Gly Ser Val Gln Ser Arg Glu Gln
                360                 365                 370 gaa cac tcc gag gca tca aag gct cga tct tca ctg gac tca gag gat        3307
Glu His Ser Glu Ala Ser Lys Ala Arg Ser Ser Leu Asp Ser Glu Asp
            375                 380                 385 gtt gaa aat aag agt aaa cca gtt tgt cat gag cag cct tct gca aca        3355
Val Glu Asn Lys Ser Lys Pro Val Cys His Glu Gln Pro Ser Ala Thr
        390                 395                 400 cct gag agt gat gca aag ggt tca gat gga gca gga gac aga aaa caa        3403
Pro Glu Ser Asp Ala Lys Gly Ser Asp Gly Ala Gly Asp Arg Lys Gln
    405                 410                 415 gtt gac cgg tcc tcg tgt ggc tca aac act ccg tcg agt agt gat gat        3451
Val Asp Arg Ser Ser Cys Gly Ser Asn Thr Pro Ser Ser Ser Asp Asp
420                 425                 430                 435 gtt gag gcg gat gca tca gaa agg caa gag gat ggc acc aat ggt gag        3499
Val Glu Ala Asp Ala Ser Glu Arg Gln Glu Asp Gly Thr Asn Gly Glu
                440                 445                 450 gtg aaa gaa acg aat gaa gac act aat aaa cct caa act tca gag tcc        3547
Val Lys Glu Thr Asn Glu Asp Thr Asn Lys Pro Gln Thr Ser Glu Ser
            455                 460                 465 aat gca cgc cgc agt aga atc agc tcc aat ata acc gat cca tgg aag        3595
Asn Ala Arg Arg Ser Arg Ile Ser Ser Asn Ile Thr Asp Pro Trp Lys
        470                 475                 480 tct gtg tct gac gag gtacttactt ggactaaaga tcaacttcct ttatttcaaa       3650
Ser Val Ser Asp Glu
            485 tcattttctc atataaatat tgtacattcg ggt cga att gcc ttc caa gct ctc       3704
                                 Gly Arg Ile Ala Phe Gln Ala Leu
                                            490                 495 ttc tcc aga gag gta ttg ccg caa agt ttt aca tat cga gaa gaa cac        3752
Phe Ser Arg Glu Val Leu Pro Gln Ser Phe Thr Tyr Arg Glu Glu His
            500                 505                 510
```

```
aga gag gaa gaa caa caa caa gaa caa aga tat cca atg gca ctt        3800
Arg Glu Glu Glu Gln Gln Gln Glu Gln Arg Tyr Pro Met Ala Leu
        515                 520                 525 gat ctt aac ttc aca gct cag tta aca cca gtt gat gat caa gag gag    3848
Asp Leu Asn Phe Thr Ala Gln Leu Thr Pro Val Asp Asp Gln Glu Glu
530                 535                 540 aag aga aac aca gga ttt ctt gga atc gga tta gat gct tca aag cta    3896
Lys Arg Asn Thr Gly Phe Leu Gly Ile Gly Leu Asp Ala Ser Lys Leu
545                 550                 555                 560 atg agt aga gga aga aca ggt ttt aaa cca tac aaa aga tgt tcc atg    3944
Met Ser Arg Gly Arg Thr Gly Phe Lys Pro Tyr Lys Arg Cys Ser Met
                565                 570                 575 gaa gcc aaa gaa agt aga atc ctc aac aac aat cct atc att cat gtg    3992
Glu Ala Lys Glu Ser Arg Ile Leu Asn Asn Asn Pro Ile Ile His Val
            580                 585                 590 gaa cag aaa gat ccc aaa cgg atg cgg ttg gaa act caa gct tcc aca    4040
Glu Gln Lys Asp Pro Lys Arg Met Arg Leu Glu Thr Gln Ala Ser Thr
        595                 600                 605 tgagactcta ttttcatctg atctgttgtt tgtactctgt ttttaagttt tcaagaccac  4100
tgctacattt tcttttctt tgaggcctt tgtatttgtt tccttgtcca tagtcttcct    4160
gtaacatttg actctgtatt attcaacaaa tcataaactg tttaatcttt ttttttccaa  4220
cctggaaaga acttcactca aggggctctt gttcttgata tatgcaaacg acagagttcc  4280
aaaacgtaat cttagcccat ccatcaccct taagttgtct cataactcat aagtaagcac  4340
aaaa                                                               4344

<210> SEQ ID NO 2
<211> LENGTH: 608
<212> TYPE: PRT
<213> ORGANISM: Arabadopsis/thalia

<400> SEQUENCE: 2

Met Glu Thr Asn Ser Ser Gly Glu Asp Leu Val Ile Lys Thr Arg Lys
1               5                   10                  15

Pro Tyr Thr Ile Thr Lys Gln Arg Glu Arg Trp Thr Glu Glu His
            20                  25                  30

Asn Arg Phe Ile Glu Ala Leu Arg Leu Tyr Gly Arg Ala Trp Gln Lys
        35                  40                  45

Ile Glu Glu His Val Ala Thr Lys Thr Ala Val Gln Ile Arg Ser His
    50                  55                  60

Ala Gln Lys Phe Phe Ser Lys Val Glu Lys Glu Ala Glu Ala Lys Gly
65                  70                  75                  80

Val Ala Met Gly Gln Ala Leu Asp Ile Ala Ile Pro Pro Pro Arg Pro
                85                  90                  95

Lys Arg Lys Pro Asn Asn Pro Tyr Pro Arg Lys Thr Gly Ser Gly Thr
            100                 105                 110

Ile Leu Met Ser Lys Thr Gly Val Asn Asp Gly Lys Glu Ser Leu Gly
        115                 120                 125

Ser Glu Lys Val Ser His Pro Glu Met Ala Asn Glu Asp Arg Gln Gln
    130                 135                 140

Ser Lys Pro Glu Glu Lys Thr Leu Gln Glu Asp Asn Cys Ser Asp Cys
145                 150                 155                 160

Phe Thr His Gln Tyr Leu Ser Ala Ala Ser Met Asn Lys Ser Cys
                165                 170                 175

Ile Glu Thr Ser Asn Ala Ser Thr Phe Arg Glu Phe Leu Pro Ser Arg
            180                 185                 190
```

```
Glu Glu Gly Ser Gln Asn Asn Arg Val Arg Lys Glu Ser Asn Ser Asp
            195                 200                 205

Leu Asn Ala Lys Ser Leu Glu Asn Gly Asn Glu Gln Gly Pro Gln Thr
            210                 215                 220

Tyr Pro Met His Ile Pro Val Leu Val Pro Leu Gly Ser Ser Ile Thr
225                 230                 235                 240

Ser Ser Leu Ser His Pro Pro Ser Glu Pro Asp Ser His Pro His Thr
                245                 250                 255

Val Ala Gly Asp Tyr Gln Ser Phe Pro Asn His Ile Met Ser Thr Leu
            260                 265                 270

Leu Gln Thr Pro Ala Leu Tyr Thr Ala Ala Thr Phe Ala Ser Ser Phe
            275                 280                 285

Trp Pro Pro Asp Ser Ser Gly Gly Ser Pro Val Pro Gly Asn Ser Pro
            290                 295                 300

Pro Asn Leu Ala Ala Met Ala Ala Ala Thr Val Ala Ala Ala Ser Ala
305                 310                 315                 320

Trp Trp Ala Ala Asn Gly Leu Leu Pro Leu Cys Ala Pro Leu Ser Ser
                325                 330                 335

Gly Gly Phe Thr Ser His Pro Pro Ser Thr Phe Gly Pro Ser Cys Asp
            340                 345                 350

Val Glu Tyr Thr Lys Ala Ser Thr Leu Gln His Gly Ser Val Gln Ser
            355                 360                 365

Arg Glu Gln Glu His Ser Glu Ala Ser Lys Ala Arg Ser Ser Leu Asp
            370                 375                 380

Ser Glu Asp Val Glu Asn Lys Ser Lys Pro Val Cys His Glu Gln Pro
385                 390                 395                 400

Ser Ala Thr Pro Glu Ser Asp Ala Lys Gly Ser Asp Gly Ala Gly Asp
                405                 410                 415

Arg Lys Gln Val Asp Arg Ser Ser Cys Gly Ser Asn Thr Pro Ser Ser
            420                 425                 430

Ser Asp Asp Val Glu Ala Asp Ala Ser Glu Arg Gln Glu Asp Gly Thr
            435                 440                 445

Asn Gly Glu Val Lys Glu Thr Asn Glu Asp Thr Asn Lys Pro Gln Thr
            450                 455                 460

Ser Glu Ser Asn Ala Arg Arg Ser Arg Ile Ser Ser Asn Ile Thr Asp
465                 470                 475                 480

Pro Trp Lys Ser Val Ser Asp Glu Gly Arg Ile Ala Phe Gln Ala Leu
                485                 490                 495

Phe Ser Arg Glu Val Leu Pro Gln Ser Phe Thr Tyr Arg Glu Glu His
            500                 505                 510

Arg Glu Glu Glu Gln Gln Gln Gln Glu Gln Arg Tyr Pro Met Ala Leu
            515                 520                 525

Asp Leu Asn Phe Thr Ala Gln Leu Thr Pro Val Asp Asp Gln Glu Glu
            530                 535                 540

Lys Arg Asn Thr Gly Phe Leu Gly Ile Gly Leu Asp Ala Ser Lys Leu
545                 550                 555                 560

Met Ser Arg Gly Arg Thr Gly Phe Lys Pro Tyr Lys Arg Cys Ser Met
                565                 570                 575

Glu Ala Lys Glu Ser Arg Ile Leu Asn Asn Asn Pro Ile Ile His Val
            580                 585                 590

Glu Gln Lys Asp Pro Lys Arg Met Arg Leu Glu Thr Gln Ala Ser Thr
            595                 600                 605
```

<210> SEQ ID NO 3
<211> LENGTH: 2254
<212> TYPE: DNA
<213> ORGANISM: Arabadopsis/thalia

<400> SEQUENCE: 3

| | | |
|---|---|---|
| tgagatttct ccatttccgt agcttctggt ctcttttctt tgtttcattg atcaaaagca | | 60 |
| aatcacttct tcttcttctt cttctcgatt tcttactgtt ttcttatcca acgaaatctg | | 120 |
| gaattaaaaa tggaatcttt atcgaatcca agctgatttt gtttctttca ttgaatcatc | | 180 |
| tctctaaagt ggaattttgt aaagagaaga tctgaagttg tgtagaggag cttagtg | | 237 |

| | | |
|---|---|---|
| atg gag aca aat tcg tct gga gaa gat ctg gtt att aag act cgg aag | | 285 |
| Met Glu Thr Asn Ser Ser Gly Glu Asp Leu Val Ile Lys Thr Arg Lys | | |
| 1               5                   10                  15 | | |
| cca tat acg ata aca aag caa cgt gaa agg tgg act gag gaa gaa cat | | 333 |
| Pro Tyr Thr Ile Thr Lys Gln Arg Glu Arg Trp Thr Glu Glu Glu His | | |
|             20                  25                  30 | | |
| aat aga ttc att gaa gct ttg agg ctt tat ggt aga gca tgg cag aag | | 381 |
| Asn Arg Phe Ile Glu Ala Leu Arg Leu Tyr Gly Arg Ala Trp Gln Lys | | |
|         35                  40                  45 | | |
| att gaa gaa cat gta gca aca aaa act gct gtc cag ata aga agt cac | | 429 |
| Ile Glu Glu His Val Ala Thr Lys Thr Ala Val Gln Ile Arg Ser His | | |
| 50                  55                  60 | | |
| gct cag aaa ttt ttc tcc aag gta gag aaa gag gct gaa gct aaa ggt | | 477 |
| Ala Gln Lys Phe Phe Ser Lys Val Glu Lys Glu Ala Glu Ala Lys Gly | | |
| 65                  70                  75                  80 | | |
| gta gct atg ggt caa gcg cta gac ata gct att cct cct cca cgg cct | | 525 |
| Val Ala Met Gly Gln Ala Leu Asp Ile Ala Ile Pro Pro Pro Arg Pro | | |
|             85                  90                  95 | | |
| aag cgt aaa cca aac aat cct tat cct cga aag acg gga agt gga acg | | 573 |
| Lys Arg Lys Pro Asn Asn Pro Tyr Pro Arg Lys Thr Gly Ser Gly Thr | | |
|         100                 105                 110 | | |
| atc ctt atg tca aaa acg ggt gtg aat gat gga aaa gag tcc ctt gga | | 621 |
| Ile Leu Met Ser Lys Thr Gly Val Asn Asp Gly Lys Glu Ser Leu Gly | | |
|     115                 120                 125 | | |
| tca gaa aaa gtg tcg cat cct gag atg gcc aat gaa gat cga caa caa | | 669 |
| Ser Glu Lys Val Ser His Pro Glu Met Ala Asn Glu Asp Arg Gln Gln | | |
| 130                 135                 140 | | |
| tca aag cct gaa gag aaa act ctg cag gaa gac aac tgt tca gat tgt | | 717 |
| Ser Lys Pro Glu Glu Lys Thr Leu Gln Glu Asp Asn Cys Ser Asp Cys | | |
| 145                 150                 155                 160 | | |
| ttc act cat cag tat ctc tct gct gca tcc tcc atg aat aaa agt tgt | | 765 |
| Phe Thr His Gln Tyr Leu Ser Ala Ala Ser Ser Met Asn Lys Ser Cys | | |
|             165                 170                 175 | | |
| ata gag aca tca aac gca agc act ttc cgc gag ttc ttg cct tca cgg | | 813 |
| Ile Glu Thr Ser Asn Ala Ser Thr Phe Arg Glu Phe Leu Pro Ser Arg | | |
|         180                 185                 190 | | |
| gaa gag gga agt cag aat aac agg gta aga aag gag tca aac tca gat | | 861 |
| Glu Glu Gly Ser Gln Asn Asn Arg Val Arg Lys Glu Ser Asn Ser Asp | | |
|     195                 200                 205 | | |
| ttg aat gca aaa tct ctg gaa aac ggt aat gag caa gga cct cag act | | 909 |
| Leu Asn Ala Lys Ser Leu Glu Asn Gly Asn Glu Gln Gly Pro Gln Thr | | |
| 210                 215                 220 | | |
| tat ccg atg cat atc cct gtg cta gtg cca ttg ggg agc tca ata aca | | 957 |
| Tyr Pro Met His Ile Pro Val Leu Val Pro Leu Gly Ser Ser Ile Thr | | |
| 225                 230                 235                 240 | | |
| agt tct cta tca cat cct cct tca gag cca gat agt cat ccc cac aca | | 1005 |
| Ser Ser Leu Ser His Pro Pro Ser Glu Pro Asp Ser His Pro His Thr | | |
|             245                 250                 255 | | |

```
gtt gca gga gat tat cag tcg ttt cct aat cat ata atg tca acc ctt    1053
Val Ala Gly Asp Tyr Gln Ser Phe Pro Asn His Ile Met Ser Thr Leu
            260                 265                 270 tta caa aca ccg gct ctt tat act gcc gca act ttc gcc tca tca ttt    1101
Leu Gln Thr Pro Ala Leu Tyr Thr Ala Ala Thr Phe Ala Ser Ser Phe
            275                 280                 285 tgg cct ccc gat tct agt ggt ggc tca cct gtt cca ggg aac tca cct    1149
Trp Pro Pro Asp Ser Ser Gly Gly Ser Pro Val Pro Gly Asn Ser Pro
            290                 295                 300 ccg aat ctg gct gcc atg gcc gca gcc act gtt gca gct gct agt gct    1197
Pro Asn Leu Ala Ala Met Ala Ala Ala Thr Val Ala Ala Ala Ser Ala
305                 310                 315                 320 tgg tgg gct gcc aat gga tta tta cct tta tgt gct cct ctt agt tca    1245
Trp Trp Ala Ala Asn Gly Leu Leu Pro Leu Cys Ala Pro Leu Ser Ser
                325                 330                 335 ggt ggt ttc act agt cat cct cca tct act ttt gga cca tca tgt gat    1293
Gly Gly Phe Thr Ser His Pro Pro Ser Thr Phe Gly Pro Ser Cys Asp
            340                 345                 350 gta gag tac aca aaa gca agc act tta caa cat ggt tct gtg cag agc    1341
Val Glu Tyr Thr Lys Ala Ser Thr Leu Gln His Gly Ser Val Gln Ser
            355                 360                 365 cga gag caa gaa cac tcc gag gca tca aag gct cga tct tca ctg gac    1389
Arg Glu Gln Glu His Ser Glu Ala Ser Lys Ala Arg Ser Ser Leu Asp
        370                 375                 380 tca gag gat gtt gaa aat aag agt aaa cca gtt tgt cat gag cag cct    1437
Ser Glu Asp Val Glu Asn Lys Ser Lys Pro Val Cys His Glu Gln Pro
385                 390                 395                 400 tct gca aca cct gag agt gat gca aag ggt tca gat gga gca gga gac    1485
Ser Ala Thr Pro Glu Ser Asp Ala Lys Gly Ser Asp Gly Ala Gly Asp
                405                 410                 415 aga aaa caa gtt gac cgg tcc tcg tgt ggc tca aac act ccg tcg agt    1533
Arg Lys Gln Val Asp Arg Ser Ser Cys Gly Ser Asn Thr Pro Ser Ser
            420                 425                 430 agt gat gat gtt gag gcg gat gca tca gaa agg caa gag gat ggc acc    1581
Ser Asp Asp Val Glu Ala Asp Ala Ser Glu Arg Gln Glu Asp Gly Thr
            435                 440                 445 aat ggt gag gtg aaa gaa acg aat gaa gac act aat aaa cct caa act    1629
Asn Gly Glu Val Lys Glu Thr Asn Glu Asp Thr Asn Lys Pro Gln Thr
450                 455                 460 tca gag tcc aat gca cgc cgc agt aga atc agc tcc aat ata acc gat    1677
Ser Glu Ser Asn Ala Arg Arg Ser Arg Ile Ser Ser Asn Ile Thr Asp
465                 470                 475                 480 cca tgg aag tct gtg tct gac gag ggt cga att gcc ttc caa gct ctc    1725
Pro Trp Lys Ser Val Ser Asp Glu Gly Arg Ile Ala Phe Gln Ala Leu
                485                 490                 495 ttc tcc aga gag gta ttg ccg caa agt ttt aca tat cga gaa gaa cac    1773
Phe Ser Arg Glu Val Leu Pro Gln Ser Phe Thr Tyr Arg Glu Glu His
            500                 505                 510 aga gag gaa gaa caa caa caa caa gaa caa aga tat cca atg gca ctt    1821
Arg Glu Glu Glu Gln Gln Gln Gln Glu Gln Arg Tyr Pro Met Ala Leu
            515                 520                 525 gat ctt aac ttc aca gct cag tta aca cca gtt gat gat caa gag gag    1869
Asp Leu Asn Phe Thr Ala Gln Leu Thr Pro Val Asp Asp Gln Glu Glu
        530                 535                 540 aag aga aac aca gga ttt ctt gga atc gga tta gat gct tca aag cta    1917
Lys Arg Asn Thr Gly Phe Leu Gly Ile Gly Leu Asp Ala Ser Lys Leu
545                 550                 555                 560 atg agt aga gga aga aca ggt ttt aaa cca tac aaa aga tgt tcc atg    1965
Met Ser Arg Gly Arg Thr Gly Phe Lys Pro Tyr Lys Arg Cys Ser Met
```

|     | 565 |     |     | 570 |     |     |     | 575 |     |     |     |     |      |
|-----|-----|-----|-----|-----|-----|-----|-----|-----|-----|-----|-----|-----|------|
| gaa | gcc | aaa | gaa | agt | aga | atc | ctc | aac | aac | aat | cct | atc | att cat gtg | 2013 |
| Glu | Ala | Lys | Glu | Ser | Arg | Ile | Leu | Asn | Asn | Asn | Pro | Ile | Ile His Val |      |
|     |     |     | 580 |     |     |     | 585 |     |     |     |     | 590 |      | gaa cag aaa gat ccc aaa cgg atg cgg ttg gaa act caa gct tcc aca     2061
Glu Gln Lys Asp Pro Lys Arg Met Arg Leu Glu Thr Gln Ala Ser Thr
          595              600              605 tgagactcta ttttcatctg atctgttgtt tgtactctgt ttttaagttt tcaagaccac     2121
tgctacattt tcttttcctt ttgaggcctt tgtatttgtt tccttgtcca tagtcttcct     2181
gtaacatttg actctgtatt attcaacaaa tcataaactg tttaatcttt tttttccaa     2241 aaaaaaaaaa aaa     2254

<210> SEQ ID NO 4
<211> LENGTH: 25
<212> TYPE: DNA
<213> ORGANISM: artificial sequence
<220> FEATURE:
<223> OTHER INFORMATION: primer

<400> SEQUENCE: 4
ctgttatgct taagaagttc aatgt     25

<210> SEQ ID NO 5
<211> LENGTH: 27
<212> TYPE: DNA
<213> ORGANISM: artificial sequence
<220> FEATURE:
<223> OTHER INFORMATION: primer

<400> SEQUENCE: 5
ccaccctcga gtagaacact tattcat     27

<210> SEQ ID NO 6
<211> LENGTH: 29
<212> TYPE: DNA
<213> ORGANISM: artificial sequence
<220> FEATURE:
<223> OTHER INFORMATION: primer

<400> SEQUENCE: 6
ggccgggatc caattcgtcg acccacgcg     29

<210> SEQ ID NO 7
<211> LENGTH: 29
<212> TYPE: DNA
<213> ORGANISM: artificial sequence
<220> FEATURE:
<223> OTHER INFORMATION: primer

<400> SEQUENCE: 7
taaagggatc catatgggtc aagcgctag     29

<210> SEQ ID NO 8
<211> LENGTH: 27 nucleotides
<212> TYPE: DNA
<213> ORGANISM: artificial sequence
<220> FEATURE:
<223> OTHER INFORMATION: primer

<400> SEQUENCE: 8
atagaattct cgagcttatg catgcgg     27

-continued

```
<210> SEQ ID NO 9
<211> LENGTH: 10
<212> TYPE: DNA
<213> ORGANISM: Arabidopsis/thalia
<220> FEATURE:
<223> OTHER INFORMATION: CCA1 binding site repeat

<400> SEQUENCE: 9 aaaraatct a                                                           10

<210> SEQ ID NO 10
<211> LENGTH: 9
<212> TYPE: DNA
<213> ORGANISM: artificial sequence
<220> FEATURE:
<223> OTHER INFORMATION: near perfect repeat

<400> SEQUENCE: 10 aaraatcta                                                              9

<210> SEQ ID NO 11
<211> LENGTH: 8
<212> TYPE: DNA
<213> ORGANISM: Arabidopsis/thalia
<220> FEATURE:
<223> OTHER INFORMATION: promoter fragment

<400> SEQUENCE: 11 aaaaatct                                                               8

<210> SEQ ID NO 12
<211> LENGTH: 24
<212> TYPE: DNA
<213> ORGANISM: artificial sequence
<220> FEATURE:
<223> OTHER INFORMATION: primer

<400> SEQUENCE: 12
gaagttgtct agaggagcta agtg                                            24

<210> SEQ ID NO 13
<211> LENGTH: 26
<212> TYPE: DNA
<213> ORGANISM: artificial sequence
<220> FEATURE:
<223> OTHER INFORMATION: primer

<400> SEQUENCE: 13
atgtggatcc ttgagtttcc aaccgc                                          26
```